(12) United States Patent
Yen et al.

(10) Patent No.: US 8,993,130 B2
(45) Date of Patent: Mar. 31, 2015

(54) ORGANIC COMPOUND AND ORGANIC ELECTROLUMINESCENT DEVICE USING THE SAME

(71) Applicant: Luminescence Technology Corporation, HsinChu (TW)

(72) Inventors: Feng-Wen Yen, Hsin-Chu (TW); Cheng-Hao Chang, Hsin-Chu (TW)

(73) Assignee: Feng-Wen Yen, Taipei (TW)

( * ) Notice: Subject to any disclaimer, the term of this patent is extended or adjusted under 35 U.S.C. 154(b) by 332 days.

(21) Appl. No.: 13/716,216

(22) Filed: Dec. 17, 2012

(65) Prior Publication Data
US 2014/0166988 A1 Jun. 19, 2014

(51) Int. Cl.
*H01L 51/50* (2006.01)
*H01L 51/00* (2006.01)

(52) U.S. Cl.
CPC ........ *H01L 51/0057* (2013.01); *H01L 51/0058* (2013.01); *H01L 51/006* (2013.01); *H01L 51/0071* (2013.01); *H01L 51/0072* (2013.01); Y10S 428/917 (2013.01)
USPC .......... 428/690; 428/917; 313/504; 313/505; 313/506; 257/40; 257/E51.05; 257/E51.026; 257/E51.032; 257/E51.052; 548/304.1; 548/418; 548/440; 548/444; 585/27

(58) Field of Classification Search
None
See application file for complete search history.

(56) References Cited

PUBLICATIONS

Lee et al., Indenofluorene-Based Fluorescent Compounds and Thier Applications in Highly Efficient Organic Light-Emitting Diodes, 2012, Eur. J. Org. Chem., pp. 2748-2755.*

* cited by examiner

*Primary Examiner* — Gregory Clark

(57) ABSTRACT

The present invention discloses a novel organic compound is represented by the following formula(I), the organic EL device employing the organic compound as host material or dopant material of emitting layer and/or as electron transporting material can lower driving voltage, prolong half-lifetime and increase the efficiency.

formula(I)

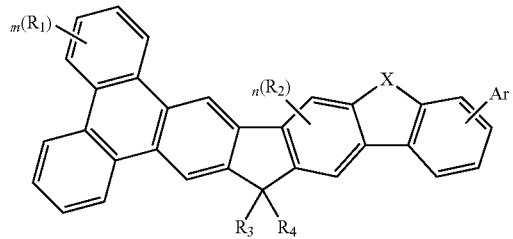

wherein m represent an integer of 0 to 10, n represent an integer of 0 to 2. X is a divalent bridge selected from the atom or group consisting from O, S, $C(R_5)_2$, $N(R_5)$, $Si(R_5)_2$. Ar, $R_1$ to $R_4$ are substituents and the same definition as described in the present invention.

9 Claims, 1 Drawing Sheet

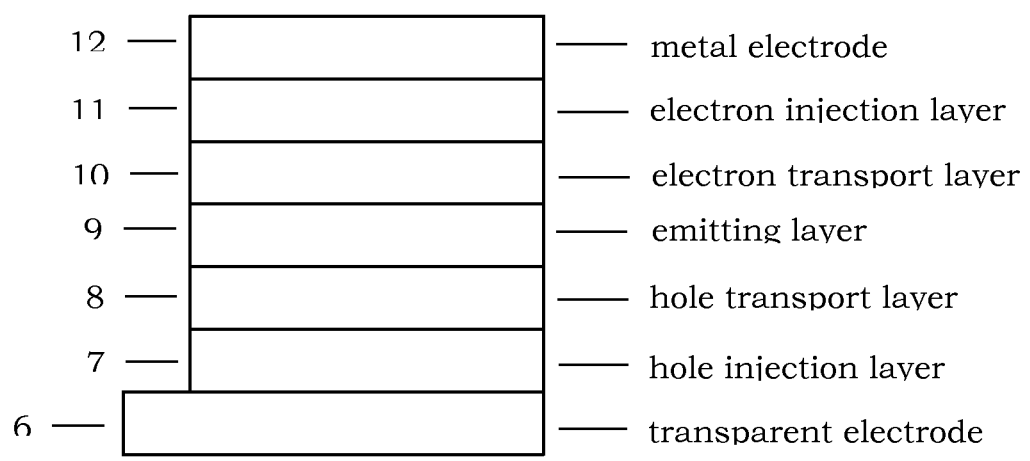

ORGANIC COMPOUND AND ORGANIC ELECTROLUMINESCENT DEVICE USING THE SAME

FIELD OF INVENTION

The present invention generally relates to a novel organic compound and organic electroluminescent (herein referred to as organic EL) device using the compound. More specifically, the present invention relates to the compound having general formula(I), an organic EL device employing the compound as host material or dopant material of emitting layer and/or as electron transporting material. Especially used as emitting layer for organic EL device.

BACKGROUND OF THE INVENTION

Organic EL device has many advantages such as self-emitting, wider viewing angles, faster response speeds and highly luminescence. Their simpler fabrication and capable of giving clear display comparable with LCD, making organic EL device an industry display of choice. Organic EL device contain emitting materials which are arranged between a cathode and a anode, when a applied driving voltage is added, an electron and a hole were injected into the emitting layer and recombined to form an exciton. The exciton which results from an electron and a hole recombination have a singlet spin state or triplet spin state. Luminescence from a singlet spin state emits fluorescence and luminescence from triplet spin state emits phosphorescence. Organic EL device are generally composed of functionally divided organic multi-layers, e.g., hole injection layer (HIL), hole transporting layer (HTL), emitting layer (EML), electron transporting layer (ETL) and electron injection layer (EIL) and so on. For full-colored flat panel displays in organic EL device, the organic compounds used for the organic multi-layer are still unsatisfactory in half-lifetime, power consumption and emitting colour. Especially for AMOLED, except prolong half-lifetime, deep blue emission (CIE y coordinates under 0.15) is necessary for improvement.

The present invention disclose a novel organic compound having general formula(I), used as host material or dopant material of emitting layer and/or as electron transporting material have excellent operational durability can lower driving voltage and power consumption, increasing efficiency and half-lifetime of organic EL device.

SUMMARY OF THE INVENTION

In accordance with the present invention, the organic compound and their use as host material or dopant material of emitting layer and/or as electron transporting material for organic EL device are provided. The material can overcome the drawbacks of the conventional materials like as shorter half-life time, lower efficiency, especially for emitting material in the present invention.

An object of the present invention is to provide the organic compound which can be used as host material or dopant material of emitting layer and/or as electron transporting material for organic EL device.

Another object of the present invention is to apply the organic compound for blue emitting material of organic EL device Another object of the present invention is to apply the organic compound for organic EL device and improve the half-lifetime, lower driving voltage, lower power consumption and increase the efficiency.

The present invention has the economic advantages for industrial practice. Accordingly, the present invention discloses the organic compound which can be used for organic EL device is disclosed. The mentioned the organic compound is represented by the following formula(I):

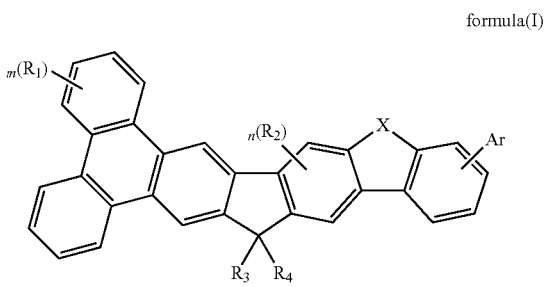

formula(I)

m represent an integer of 0 to 10, n represent an integer of 0 to 2. X is a divalent bridge selected from the atom or group consisting from O, S, $C(R_5)_2$, $N(R_5)$, $Si(R_5)_2$. Ar represent a hydrogen atom, a halide, a substituted or unsubstituted arylamine group, a substituted or unsubstituted aryl group system having 5 to 50 aromatic ring atoms, a substituted or unsubstituted heteroaryl ring system having 5 to 50 aromatic ring atoms and each aromatic ring to form a mono or polycyclic ring system. $R_1$ to $R_5$ are identical or different. $R_1$ to $R_5$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

According to the present invention, the organic compound formula(I) preferably used as fluorescent emitting material or dopant is represented by the following formula(II):

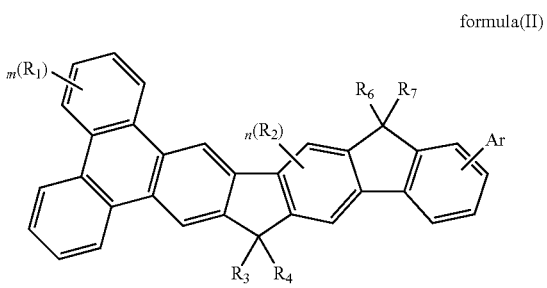

formula(II)

m represent an integer of 0 to 10, n represent an integer of 0 to 2. Ar represent a hydrogen atom, a halide, a substituted or unsubstituted arylamine group, a substituted or unsubstituted aryl group system having 5 to 50 aromatic ring atoms, a substituted or unsubstituted heteroaryl ring system having 5 to 50 aromatic ring atoms and each aromatic ring to form a mono or polycyclic ring system. $R_1$ to $R_4$ and $R_6$ to $R_7$ are identical or different. $R_1$ to $R_4$ and $R_6$ to $R_7$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. The preferable Ar group represented as the following:

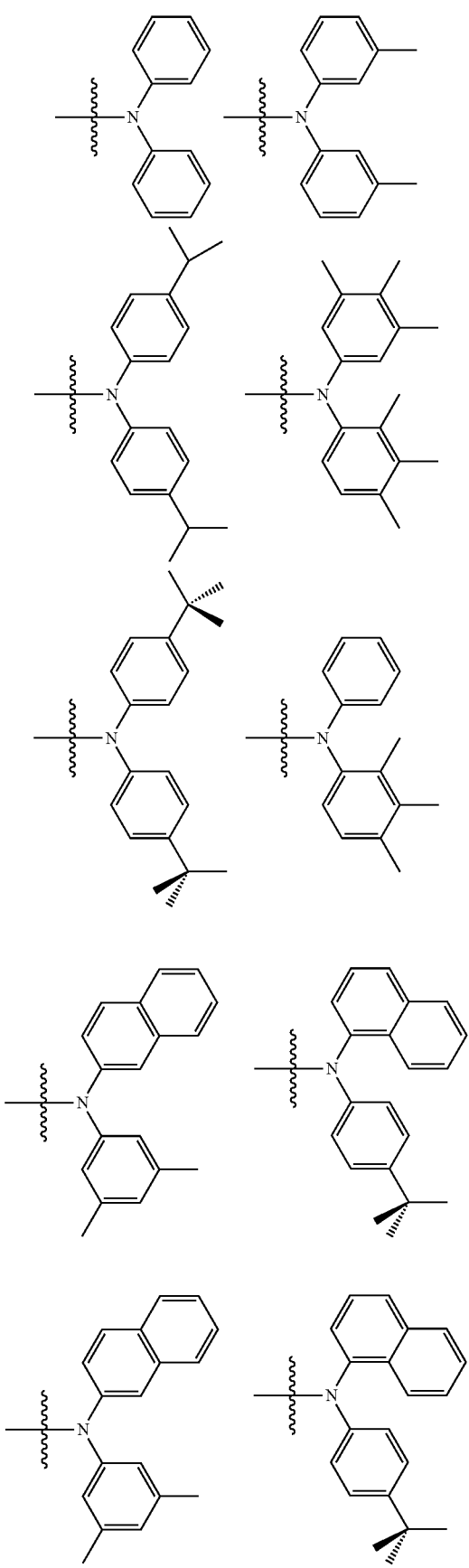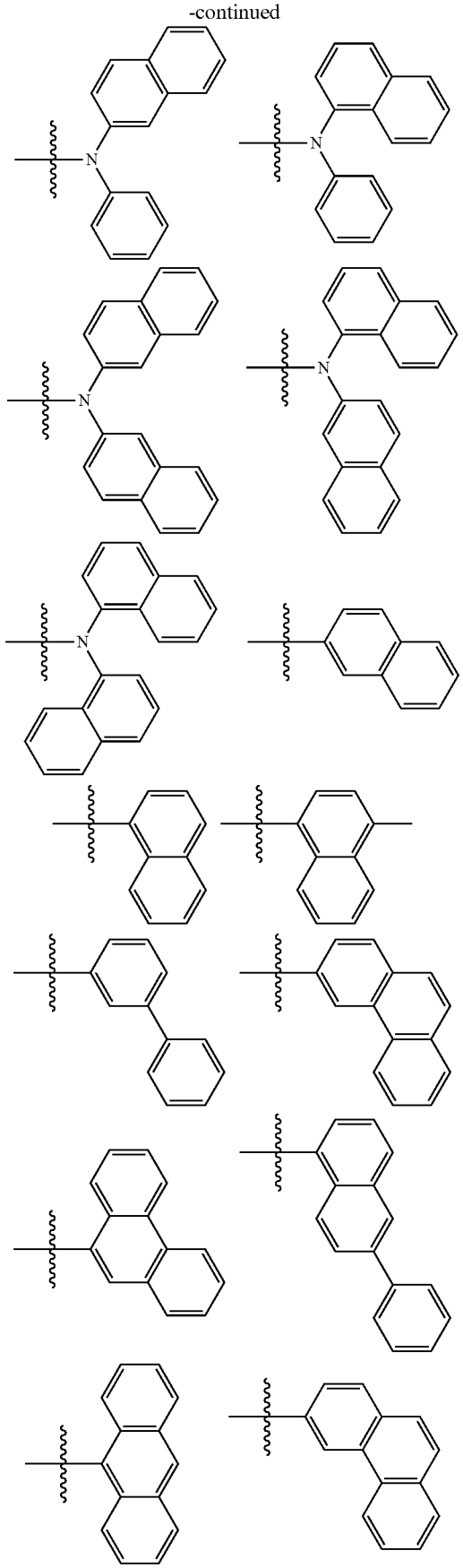

-continued

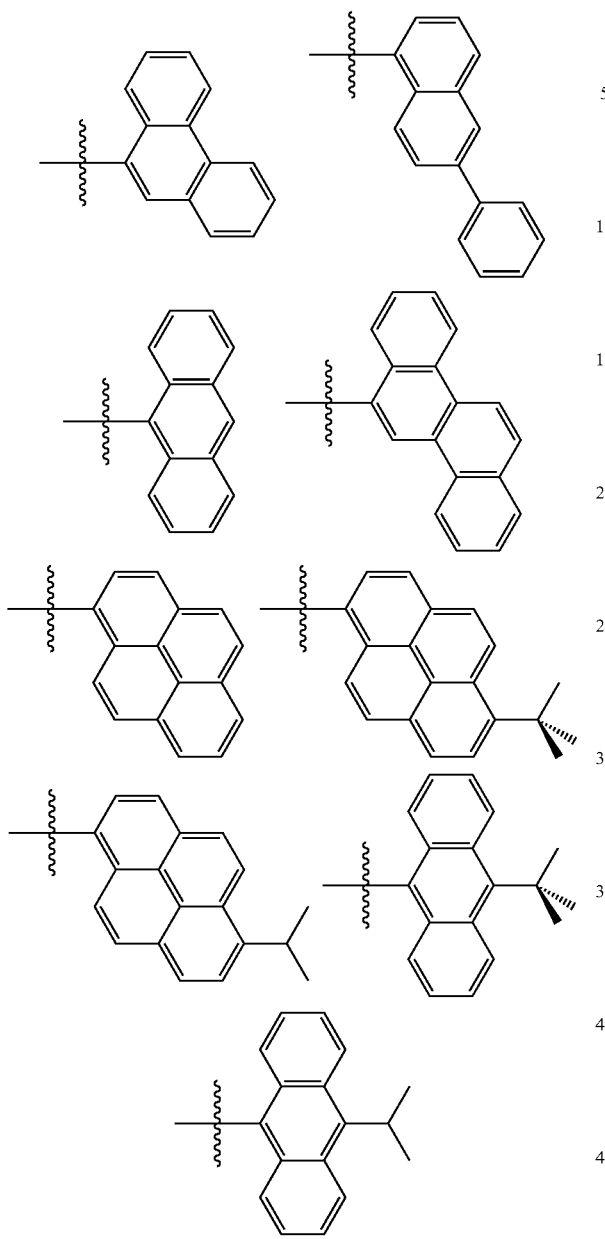

According to the present invention, the organic compound formula(I) preferably used as phosphorescent host material is represented by the following formula(III):

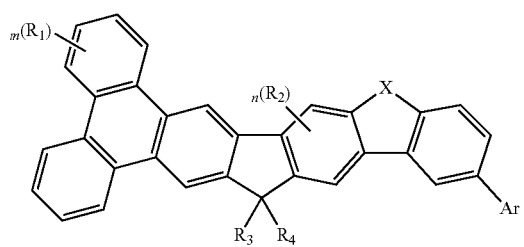

formula(III)

wherein m represent an integer of 0 to 10, n represent an integer of 0 to 2. X is a divalent bridge selected from the atom or group consisting from O, S, N(R$_5$). Ar represented a substituted or unsubstituted aryl group system having 5 to 50 aromatic ring atoms, a substituted or unsubstituted heteroaryl ring system having 5 to 50 aromatic ring atoms to form a mono or polycyclic ring system. R$_1$ to R$_5$ are identical or different. R$_1$ to R$_5$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. The preferable Ar or R$_5$ group are represented as the following:

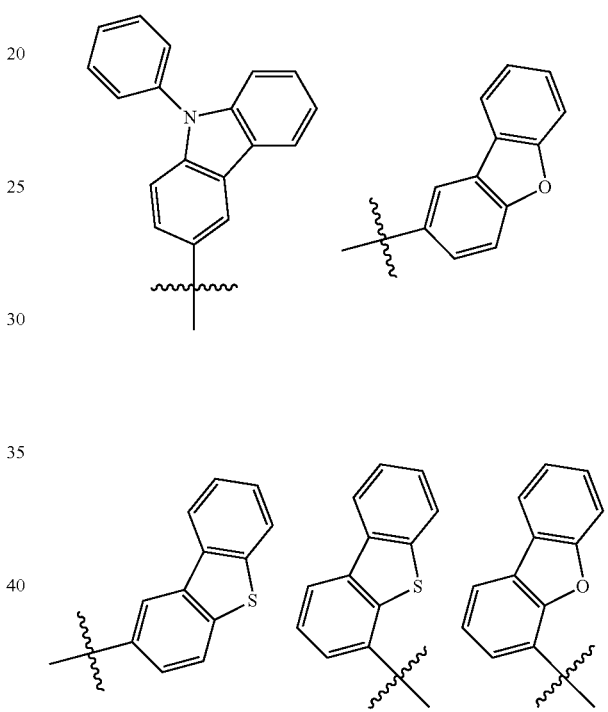

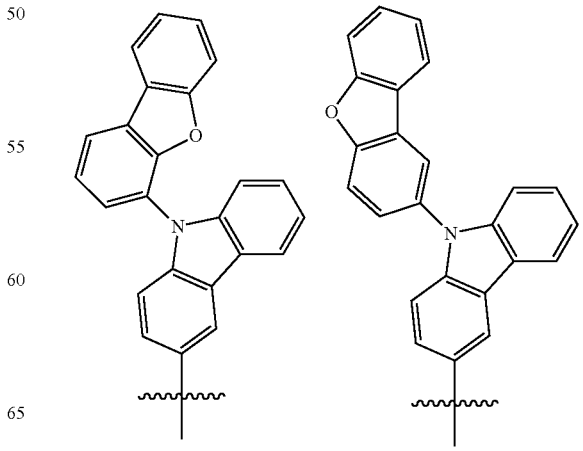

-continued

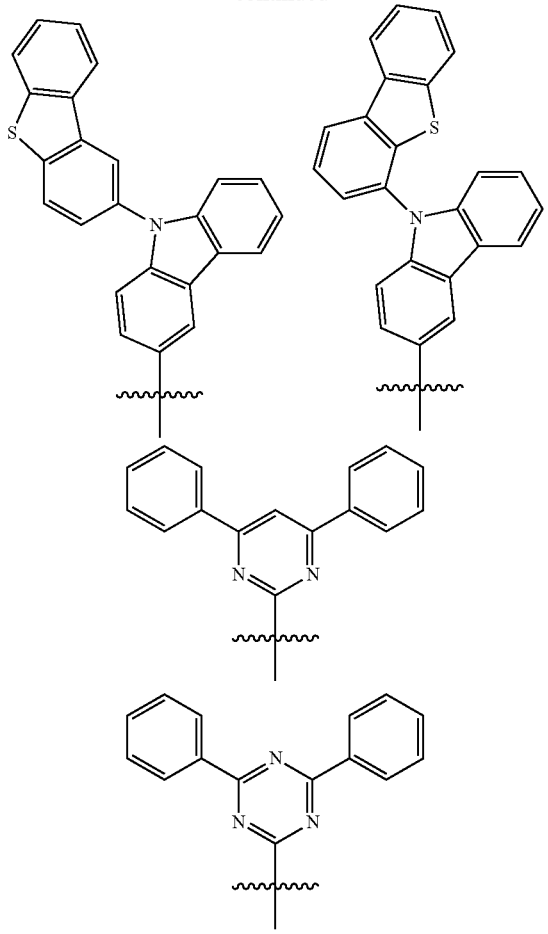

BRIEF DESCRIPTION OF THE DRAWINGS

FIG. 1 show one example of organic EL device in the present invention. 6 is transparent electrode, 12 is metal electrode, 7 is hole injection layer which is deposited onto 6, 8 is hole transporting layer which is deposited onto 7, 9 is fluorescent emitting layer which is deposited onto 8, 10 is electron transporting layer which is deposited onto 9, 11 is electron injection layer which is deposited onto 10.

DESCRIPTION OF THE PREFERRED EMBODIMENTS

What probed into the invention is the organic compound and organic EL device using the organic compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

DEFINITION

In a first embodiment of the present invention, the organic compound which can be used as host material or dopant material of emitting layer and/or as electron transporting material of organic EL device are disclosed. The mentioned organic compound are represented by the following formula (I):

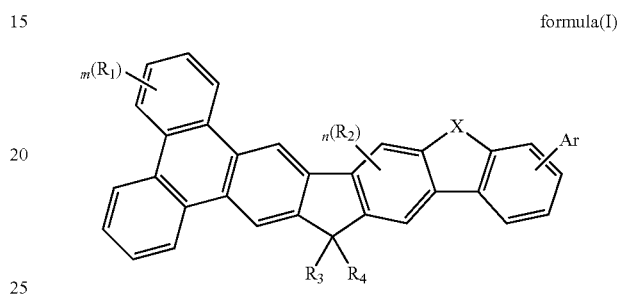

formula(I)

m represent an integer of 0 to 10, n represent an integer of 0 to 2. X is a divalent bridge selected from the atom or group consisting from O, S, $C(R_5)_2$, $N(R_5)$, $Si(R_5)_2$. Ar represent a hydrogen atom, a halide, a substituted or unsubstituted arylamine group, a substituted or unsubstituted aryl group system having 5 to 50 aromatic ring atoms, a substituted or unsubstituted heteroaryl ring system having 5 to 50 aromatic ring atoms and each aromatic ring to form a mono or polycyclic ring system. $R_1$ to $R_5$ are identical or different. $R_1$ to $R_5$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

According to the present invention, the organic compound formula(I) preferably used as fluorescent emitting material or dopant is represented by the following formula(II):

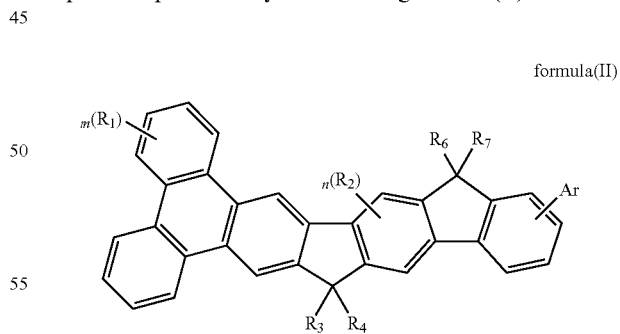

formula(II)

m represent an integer of 0 to 10, n represent an integer of 0 to 2. Ar represent a hydrogen atom, a halide, a substituted or unsubstituted arylamine group, a substituted or unsubstituted aryl group system having 5 to 50 aromatic ring atoms, a substituted or unsubstituted heteroaryl ring system having 5 to 50 aromatic ring atoms and each aromatic ring to form a mono or polycyclic ring system. $R_1$ to $R_4$ and $R_6$ to $R_7$ are identical or different. $R_1$ to $R_4$ and $R_6$ to $R_7$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. The preferable Ar group represented as the following:
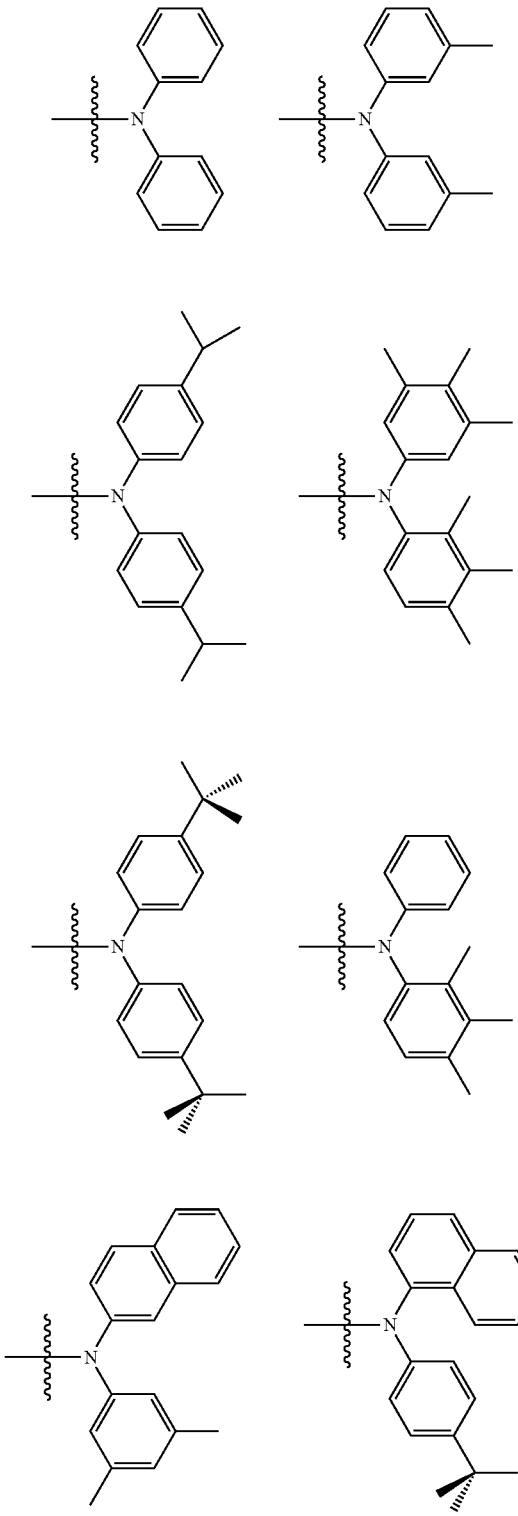
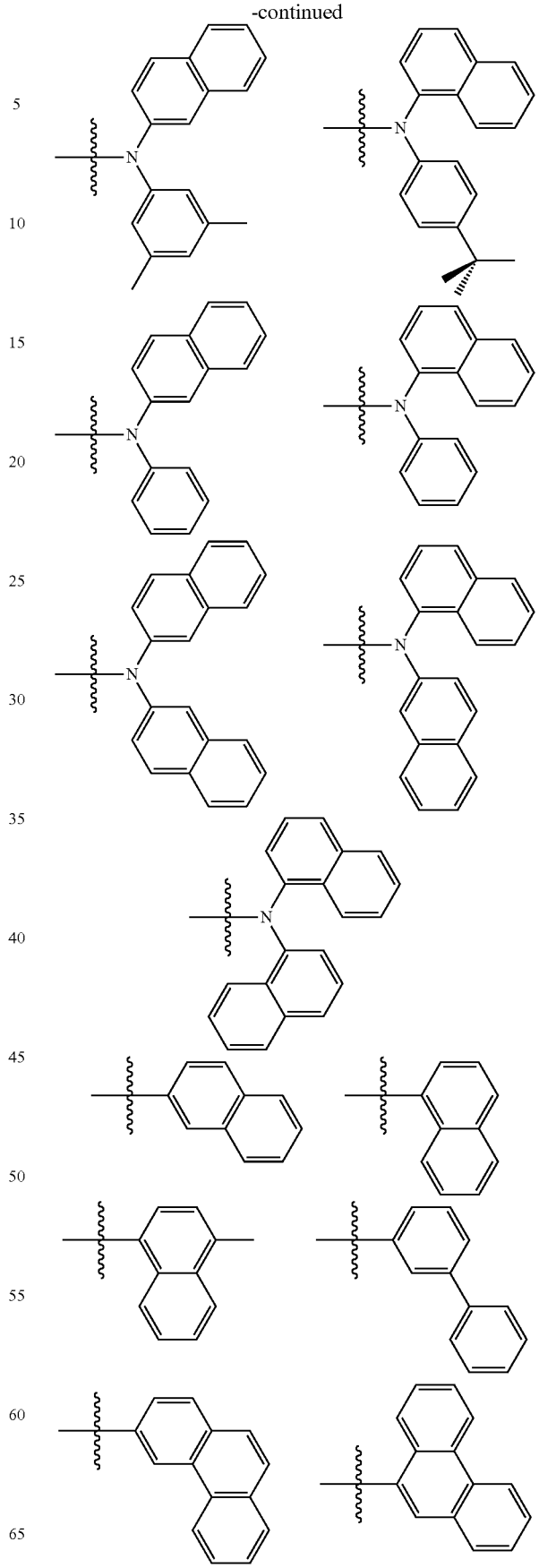

-continued

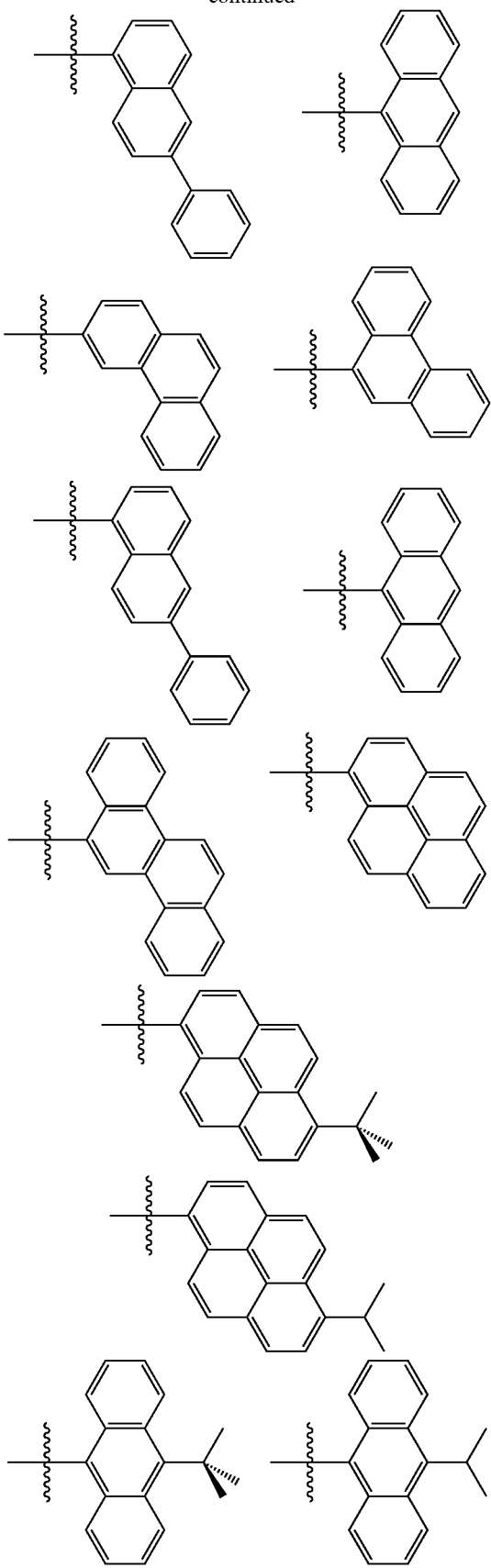

According to the present invention, the organic compound formula(I) preferably used as phosphorescent host material is represented by the following formula(III):

formula(III)

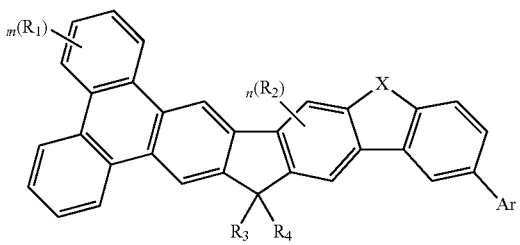

wherein m represent an integer of 0 to 10, n represent an integer of 0 to 2. X is a divalent bridge selected from the atom or group consisting from O, S, N($R_5$). Ar represented a substituted or unsubstituted aryl group system having 5 to 50 aromatic ring atoms, a substituted or unsubstituted heteroaryl ring system having 5 to 50 aromatic ring atoms to form a mono or polycyclic ring system. $R_1$ to $R_5$ are identical or different. $R_1$ to $R_5$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms. The preferable Ar or $R_5$ group are represented as the following:

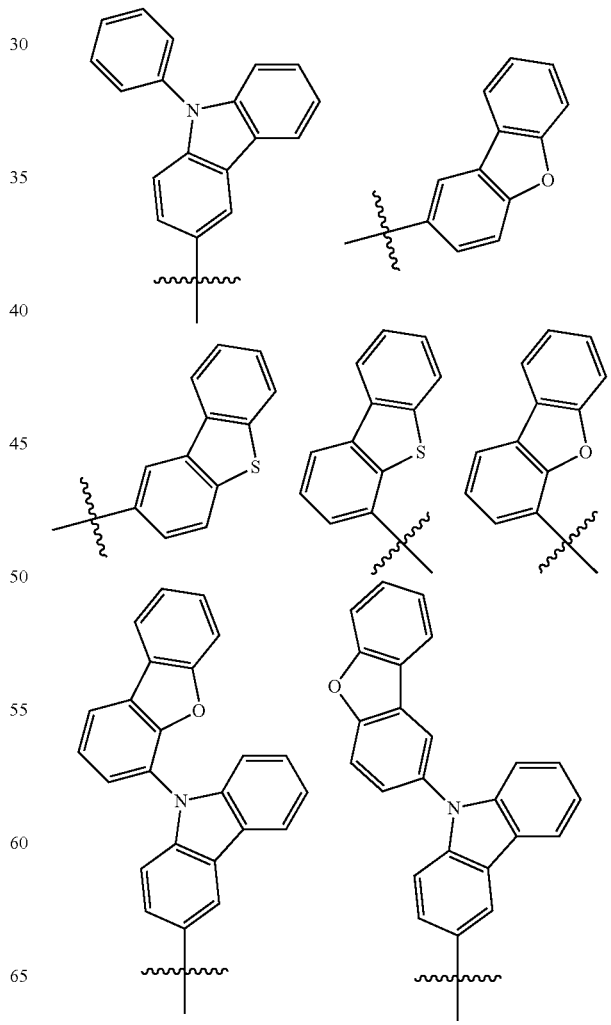

-continued
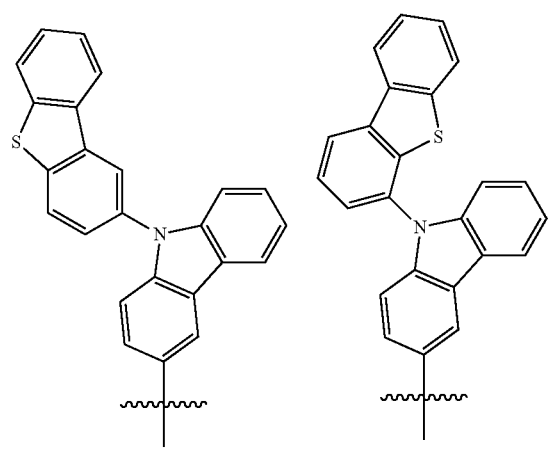
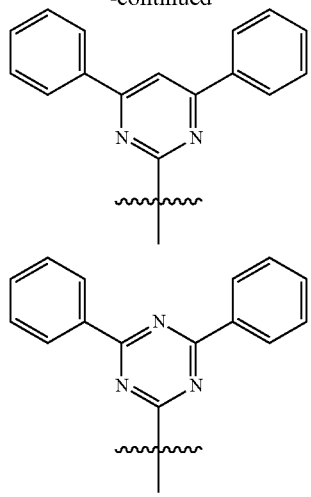
In this embodiment, some organic compounds are shown below:
II-1
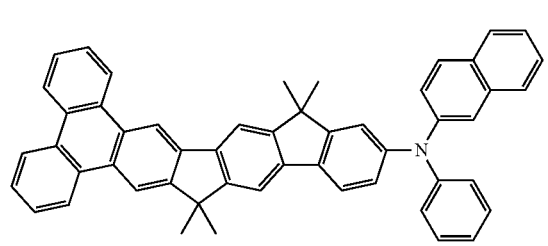
II-2
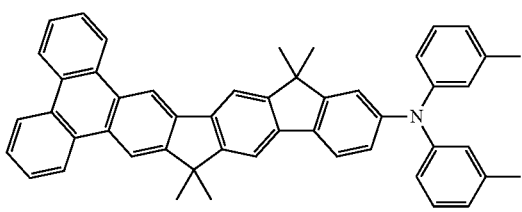
II-3
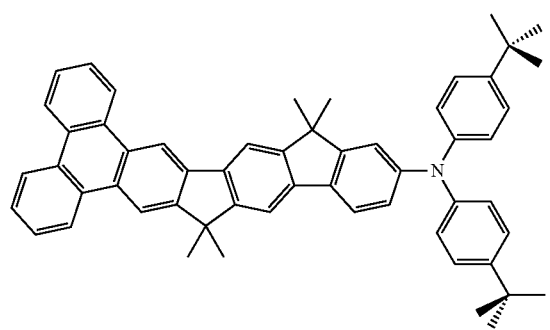
II-4
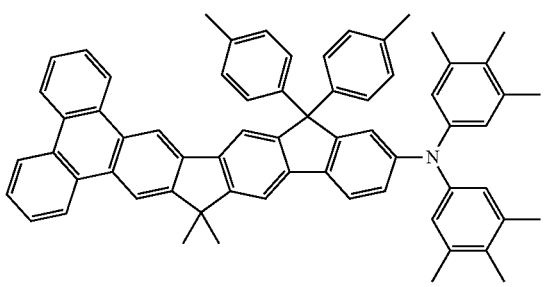
II-5
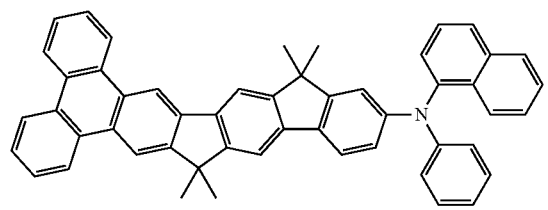
II-6
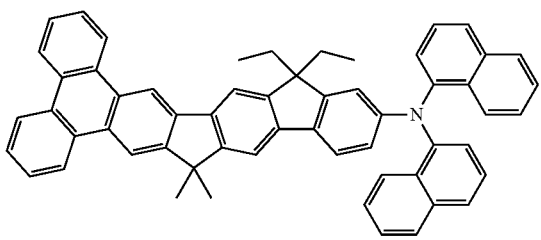

-continued
II-7
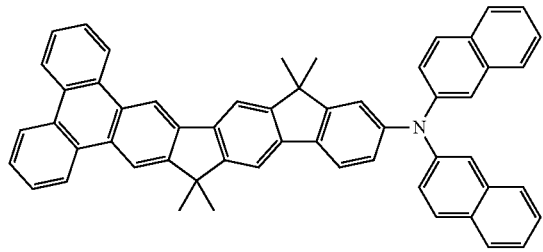
II-8
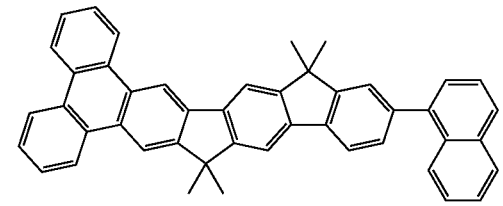
II-9
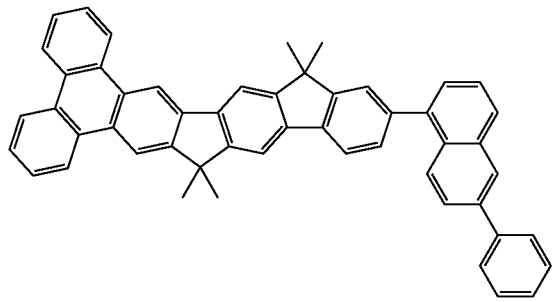
II-10
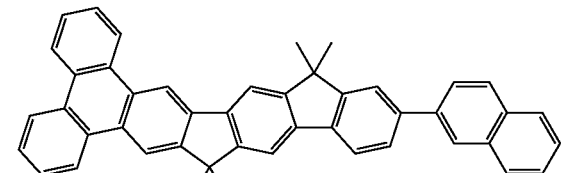
II-11
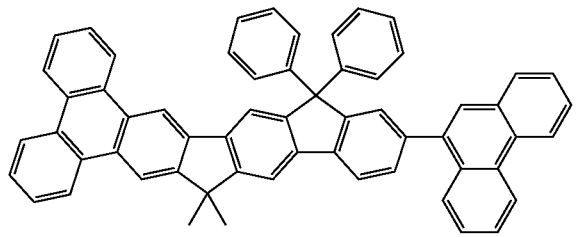
II-12
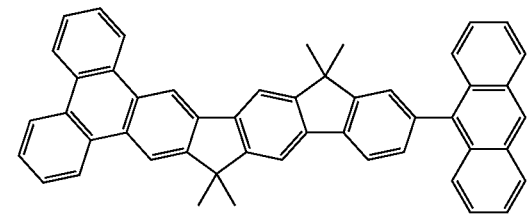
II-13
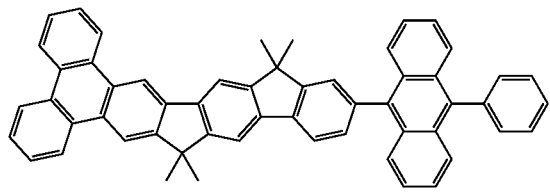
II-14
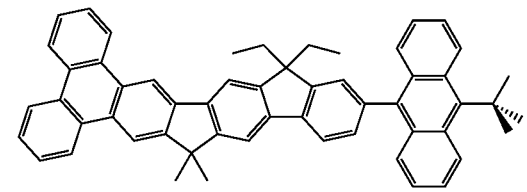
II-15
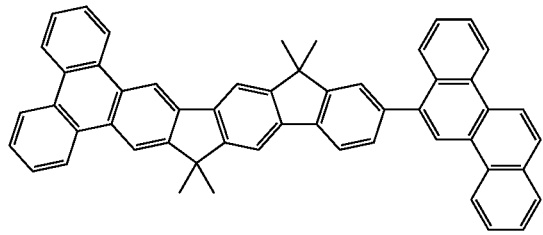
II-16
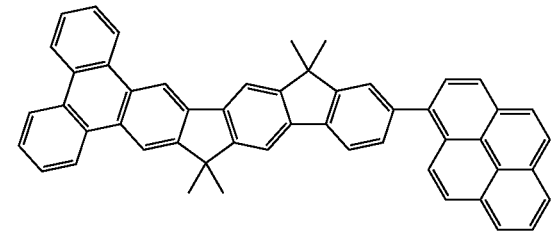
II-17
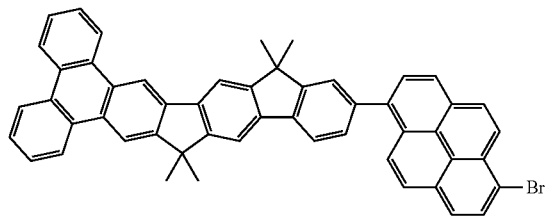
II-18
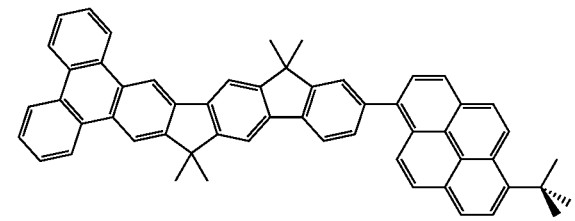

-continued
II-19
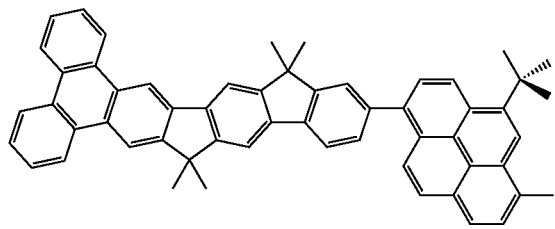
III-1
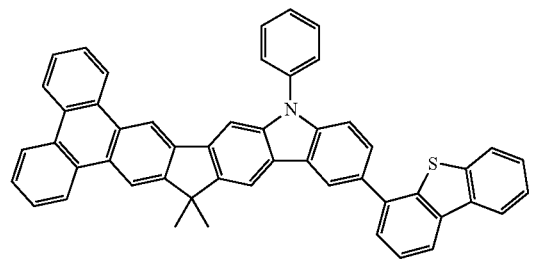
III-2
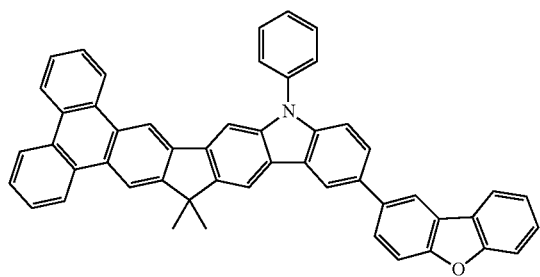
III-3
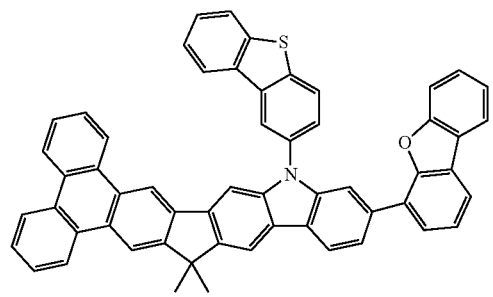
III-4
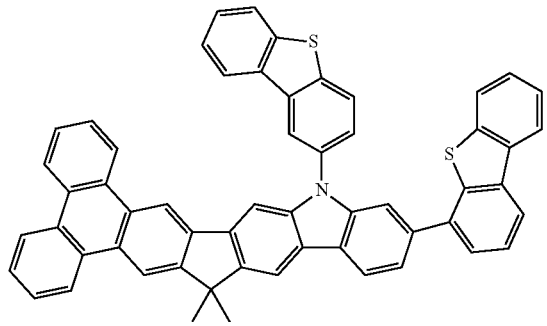
III-5
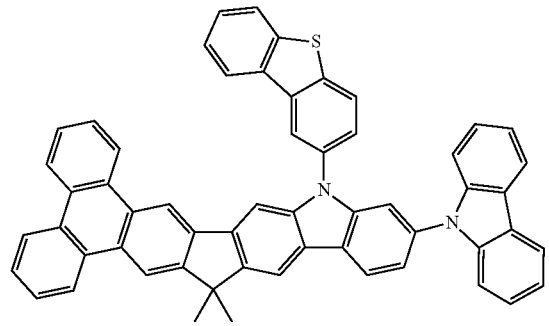
III-6
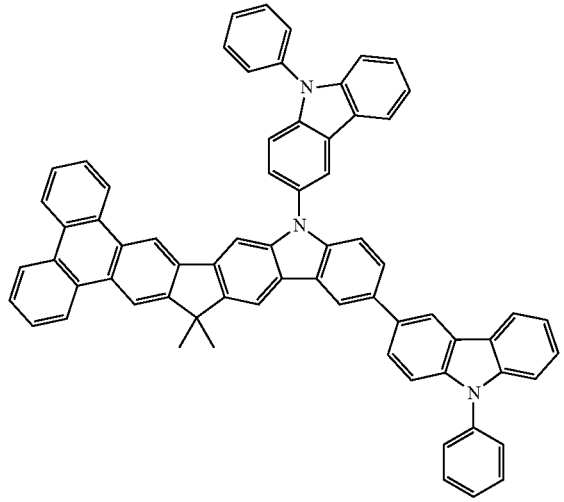
III-7
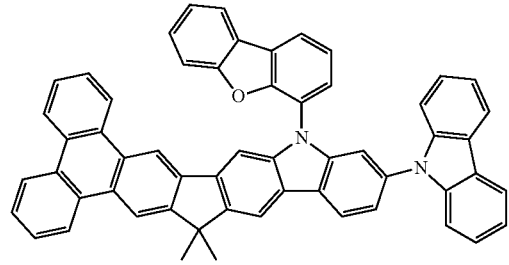

-continued
III-8
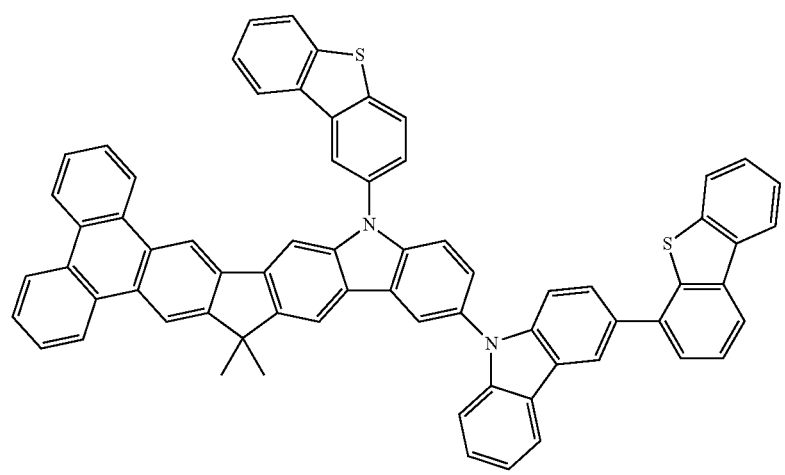
III-9
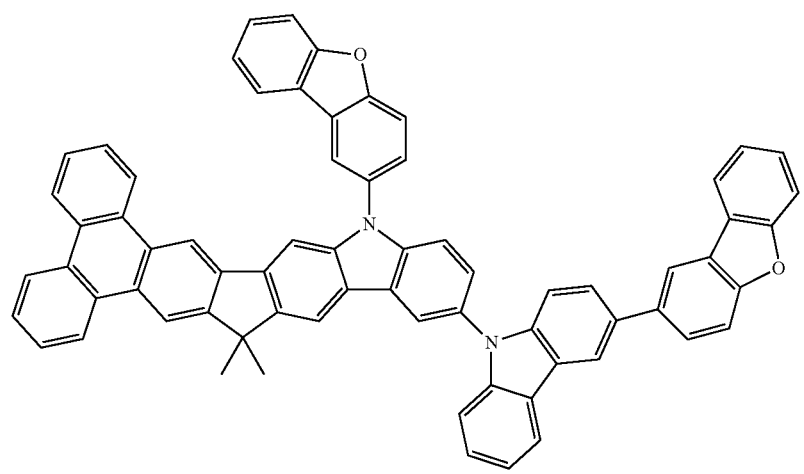
III-10
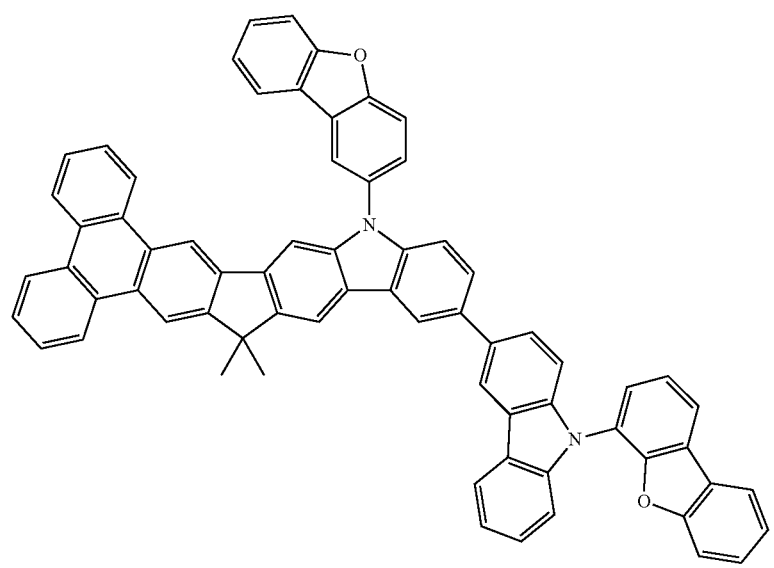

-continued
III-11
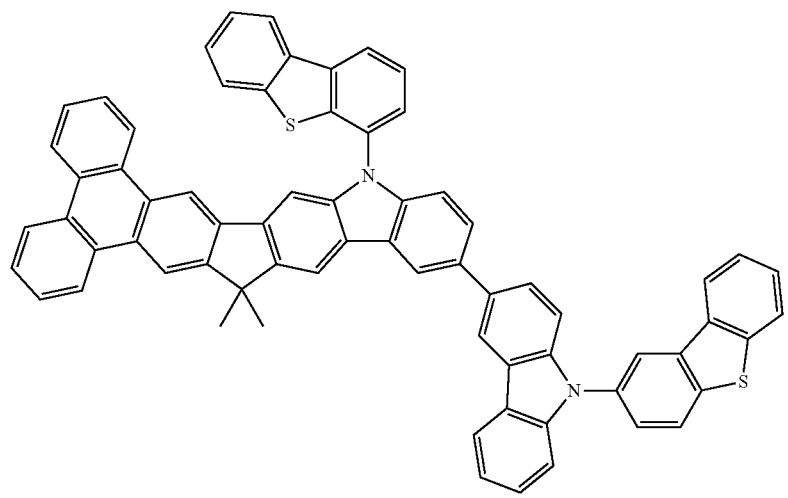
III-12
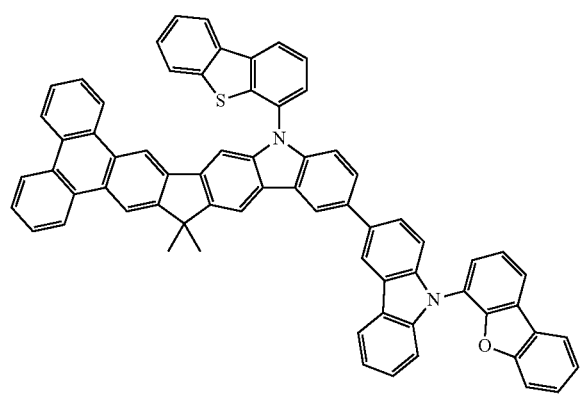
III-13
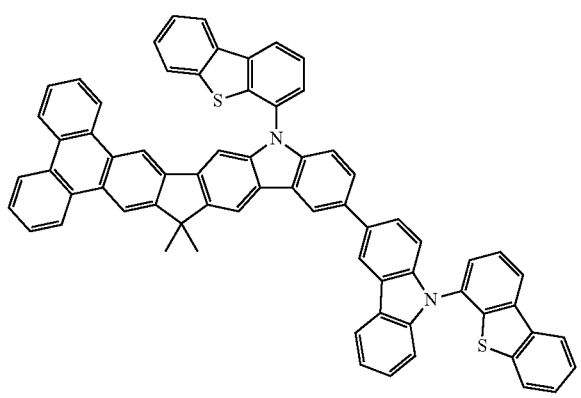
III-14
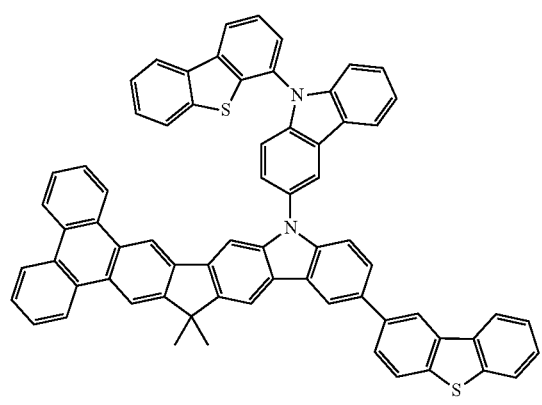
III-15
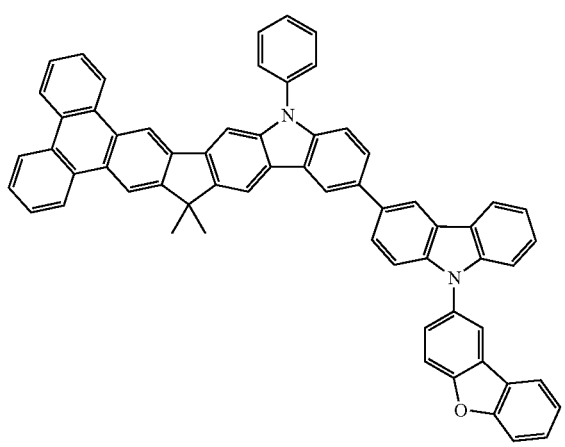

-continued
III-16
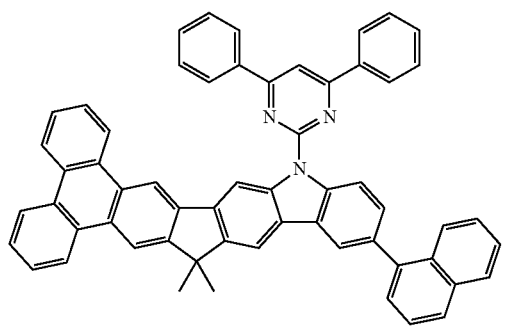
III-17
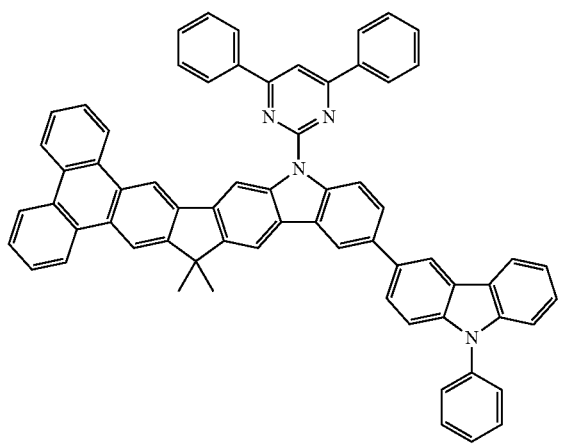
III-18
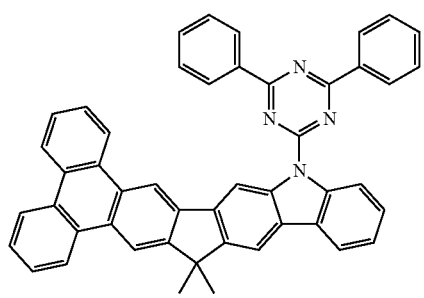
III-19
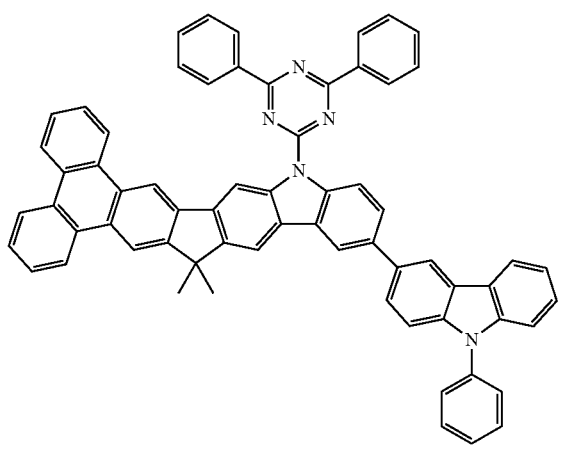
III-20
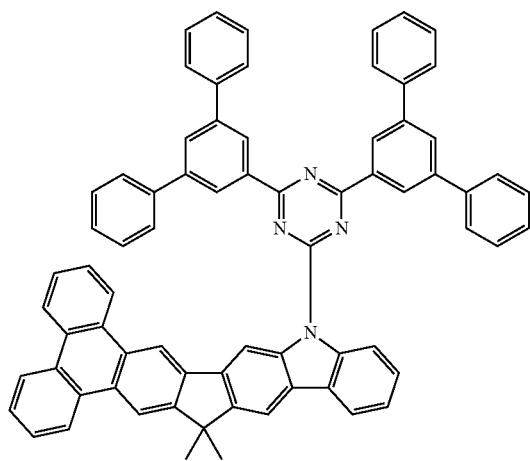
III-21
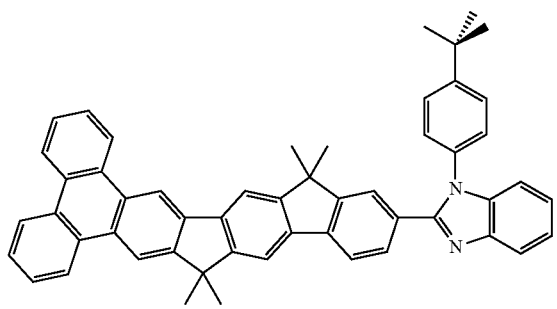

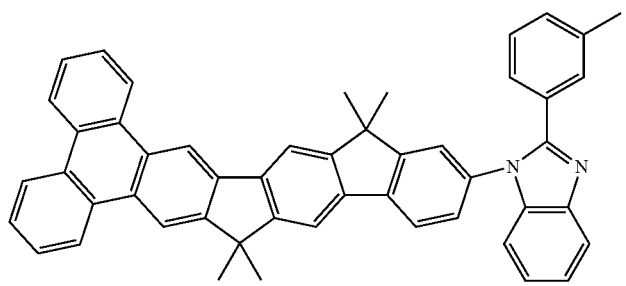

Detailed preparation for formula(I)~formula(III) could be clarified by exemplary embodiments, but the present invention is not limited to exemplary embodiments.

EXAMPLE 1

Synthesis of Compound II-2

Synthesis of 1,4-diphenyl-2,5-dimethylbenzene

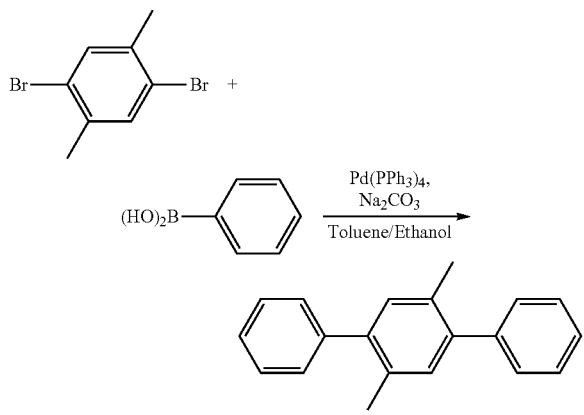

A mixture of 52.8 g (200 mmol) of 1,4-dibromo-2,5-Dimethyl benzene, 53.6 g (440 mmol) of phenylboronic acid, 2.3 g (2 mmol) of tetrakis(triphenylphosphine)palladium, 400 ml of 2M $Na_2CO_3$, 400 ml of EtOH and 800 ml toluene was degassed and placed under nitrogen, and then heated at 90° C. for 6 hours. After the reaction finish, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 43.4 g (168 mmol, 84%) as a white solid.

Synthesis of 2,5-diphenylterephthalicacid

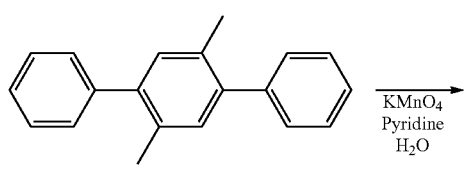

-continued

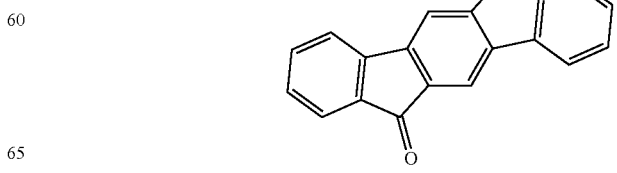

To a solution of 1,4-diphenyl-2,5-dimethylbenzene 43.4 g (168 mmol) in pyridine (450 ml) was added a hot $KMnO_4$ solution (239 g in 700 ml $H_2O$) over 1 h under reflux and the reaction was stirred at 130° C. for 12 h. After cooling to room temperature, the reaction was filtered and the residue was washed with hot $H_2O$ and ethyl acetate. The aqueous layer was acidified with 3 N HCl to pH~1 and the white suspension was extracted with ethyl acetate. After removal of solvent, a white solid was obtained which was suspended in $H_2O$ (400 mL) and treated with KOH (20 g). The solution was heated to 90° C. followed by addition of $KMnO_4$ solution (80 g in 300 ml $H_2O$) over 0.5 h. This solution was stirred for another 8 hours. After cooling to room temperature, MeOH was added and the reaction was stirred till the purple color disappeared. The mixture was filtered. Removal of filtrate afforded a white solid which was treated with 3 N HCl to pH~1. The resultant slurry was extracted with ethyl acetate. The combined organic layer was washed with brine and dried over anhydrous magnesium sulfate. After removal of solvent a white solid was obtained as the 2,5-diphenylterephthalicacid 23 g (72 mmol, 44%).

Synthesis of indeno[1,2-b]fluorene-6,12-dione

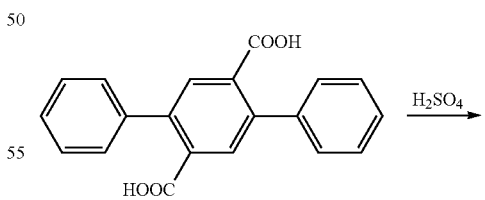

A mixture of 2,5-diphenylterephthalicacid 23 g (72 mmol), 230 ml of sulfuric acid was placed under nitrogen, and then heated to 60° C. for 1 hour. After the reaction finish, the mixture was allowed to cool to room temperature. The reaction mixture was poured on ice, the separated precipitate was filtered off, washed with water, and dried in air at room temperature to give product 17 g (60 mmol, 84%) as a yellow solid.

Synthesis of 6,12-dihydroindeno[1,2-b]fluorene

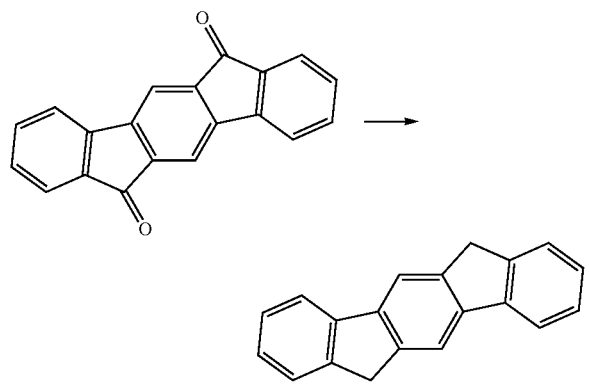

A mixture of 17 g (60 mmol) of indeno[1,2-b]fluorene-6, 12-dione, 18 g (600 mmol) of hydrazine monohydrate in 350 ml of diethylene glycol was stirred at 80° C. for 3 hours and then refluxed for 1 hour. The resulting mixture was cooled to room temperature, treated with a solution of 33 g (590 mmol) of KOH in 90 mL of water, and refluxed for 3 hours. The resulting mixture was poured into 800 ml of water, and the precipitate was filtered off, washed with water, and dried in air at room temperature to give product 13.1 g (51.6 mmol, 86%) as a yellow solid.

Synthesis of 6,6,12,12-tetramethyl-6,12-dihydroindeno[1,2-b]fluorene

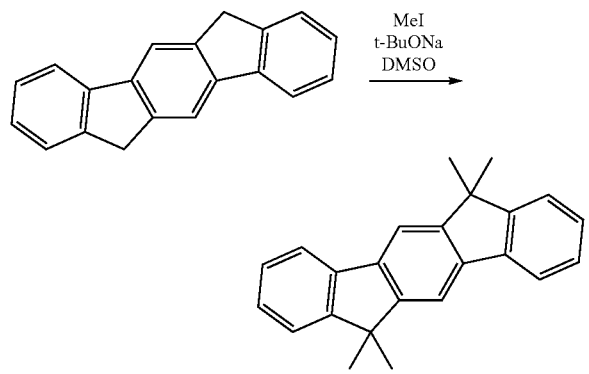

To a solution of 6,12-dihydroindeno[1,2-b]fluorene 13.1 g (51.6 mmol) and potassium iodide 4.3 g (26 mmol) in DMSO (500 ml) were added iodomethane 154 g (1084 mmol) and potassium hydroxide 61 g (1084 mmol). The reaction mixture was stirred at room temperature for 24 hours. The organic layer was separated and the aqueous layer extracted with ethyl acetate and water, dried with anhydrous magnesium sulfate, the solvent was removed and the residue was purified by column chromatography on silica (hexane-dichloromethane) to give product 8.8 g (34.6 mmol, 67%) as a yellow solid.

Synthesis of 2,8-dibromo-6,6,12,12-tetramethyl-6, 12-dihydroindeno[1,2-b]fluorene

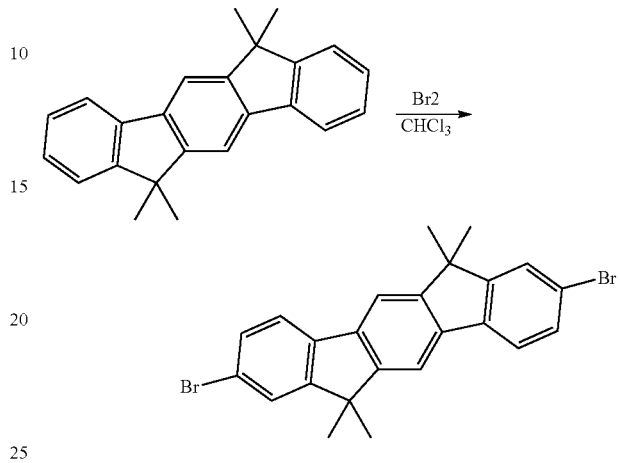

6,6,12,12-tetramethyl-6,12-dihydroindeno[1,2-b]fluorine 8.8 g (34.6 mmol) was dissolved in 100 ml chloroform, protected from light and bromine 11.6 g (72.6 mmol) diluted in 30 ml chloroform was added drop-wise at 0° C. The reaction was stirred at room temperature for 24 h, after which water (600 ml) was added. The crude product precipitated, this was filtered off and recrystallized from chloroform and methanol to give the pure product 14.7 g (31.5 mmol, 91%) as yellow solid.

Synthesis of 2-(biphenyl-2-yl)-8-bromo-6,6,12,12-Tetramethyl-6,12-dihydroindeno[1,2-b]fluorene

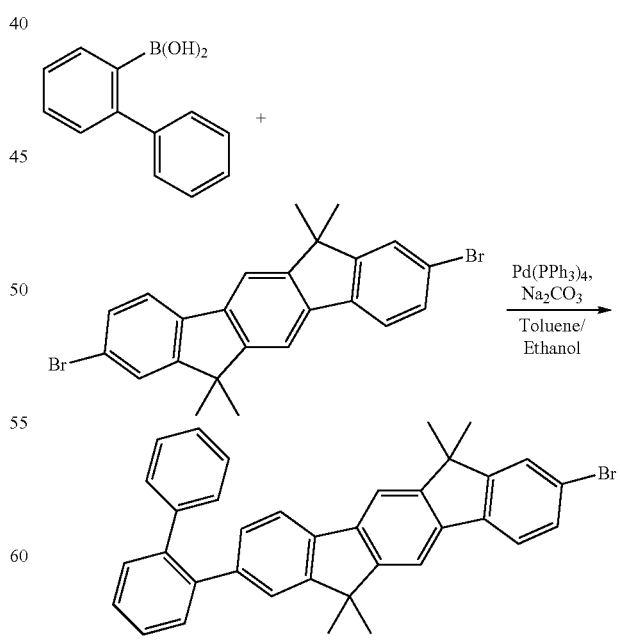

A mixture of 14.7 g (31.5 mmol) of 2,8-dibromo-6,6,12, 12-tetramethyl-6,12-dihydroindeno[1,2-b]fluorene, 6.5 g (33 mmol) of biphenyl-2-ylboronic acid, 0.36 g (0.3 mmol) of tetrakis(triphenylphosphine) palladium, 32 ml of 2M Na₂CO₃, 60 ml of EtOH and 150 ml toluene was degassed and placed under nitrogen, and then heated at 100° C. for 24 h. After finishing the reaction, the mixture was allowed to cool to room temperature. The organic layer was extracted with ethyl acetate and water, dried with anhydrous magnesium sulfate, the solvent was removed and the residue was purified by column chromatography on silica (hexane-dichloromethane) to give product 9.7 g (17.9 mmol, 57%). ¹H NMR (CDCl₃, 400 MHz): chemical shift (ppm): 7.78 (d, J=8.0 Hz, 1H), 7.65~7.61 (m, 1H), 7.56 (d, J=8.0 Hz, 1H), 7.51~7.21 (m, 10H), 7.18 (s, 2H), 7.08~6.99 (m, 2H), 1.83 (s, 6H), 1.81 (s, 6H)

Synthesis of Intermediate I

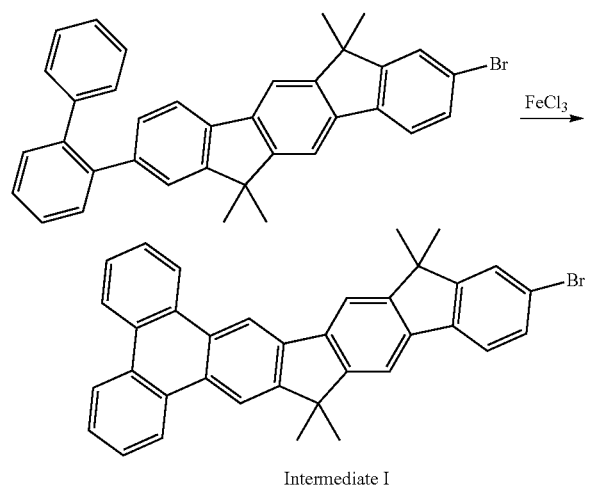

Intermediate I

In a 2000 ml three-necked flask that had been deaerated and filled with nitrogen, 9.7 g (17.9 mmol) of 2-(biphenyl-2-yl)-8-bromo-6,6,12,12-tetramethyl-6,12-dihydroindeno[1,2-b]fluorene was dissolved in anhydrous dichloromethane (600 ml), 29 g (179 mmol) Iron(III) chloride was then added, and the mixture was stirred one hour. Methanol 200 ml were added to the mixture and the organic layer was separated and the solvent removed in vacuo. The residue was purified by column chromatography on silica (hexane-dichloromethane) to afforded a yellow solid 7.5 g (14 mmol, 78%). ¹H NMR (CDCl₃, 400 MHz): chemical shift (ppm) 9.04 (s, 1H), 8.87~8.78 (m, 2H), 8.54 (s, 1H), 8.35 (d, J=8.0 Hz, 1H), 8.13 (d, J=8.0 Hz, 1H), 8.02~7.85 (m, 5H), 7.44~7.36 (m, 3H), 7.11 (d, J=8.0 Hz, 1H), 1.83 (s, 6H), 1.81 (s, 6H).

Synthesis of Intermediate II

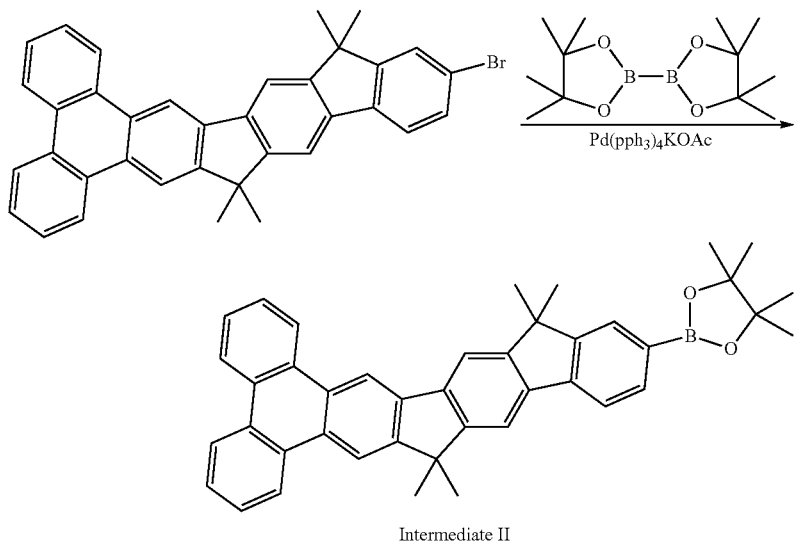

Intermediate II

A mixture of 7.5 g (14 mmol) of Intermediate I, 5.3 g (21 mmol) of bis(pinacolato)diboron, 0.3 g (0.26 mmol) of tetrakis(triphenylphosphine) palladium, 2.7 g (28 mmol) of potassium acetate, and 300 ml 1,4 dioxane was degassed and placed under nitrogen, and then heated at 90° C. for 24 hours. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product 7 g (12 mmol, 86%) as a yellow solid.

Synthesis of Compound II-2

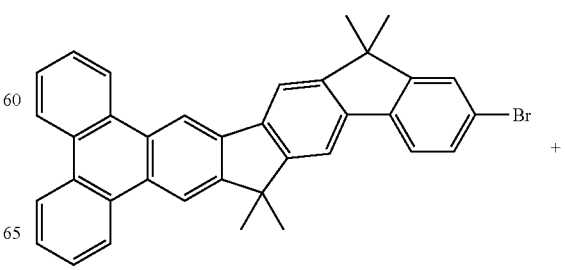

-continued

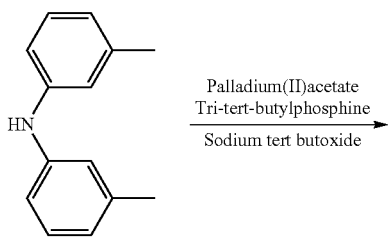

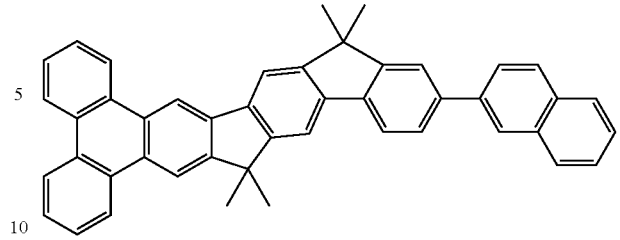

A mixture of 2.1 g (10 mmol) of 2-bromonaphthalene, 7 g (12 mmol) of Intermediate II, 0.12 g (0.1 mmol) of tetrakis(triphenylphosphine)palladium, 10 ml of 2M $Na_2CO_3$, 30 ml of EtOH and 100 ml toluene was degassed and placed under nitrogen, and then heated at 90° C. for 12 h. After finishing the reaction, the mixture was allowed to cool to room temperature. Than 500 ml MeOH was added, while stirring and the precipitated product was filtered off with suction. To give 4 g (yield 69%) of yellow product which was recrystallized from toluene. MS (m/z, $FAB^+$): 586.4; $^1H$ NMR ($CDCl_3$, 400 MHz): chemical shift (ppm) 9.11 (s, 1H), 8.76~8.68 (m, 2H), 8.61 (s, 1H), 8.35 (d, J=8.0 Hz, 1H), 8.08~7.94 (m, 2H), 7.86~7.61 (m, 5H), 7.55~7.42 (m, 6H), 7.31~7.26 (m, 2H), 7.13 (s, 1H), 7.04 (s, 1H), 1.82 (s, 6H), 1.80 (s, 6H).

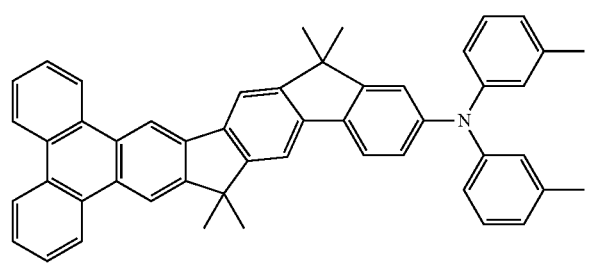

A mixture of 7 g (12 mmole) Intermediate I, 2.4 g (12 mmole) of dim-tolylamine, 0.05 g (0.6 mmole) of palladium (II)acetate, 0.24 g (1.2 mmole) of tri-tert-butylphosphine, 2.3 g (24 mmole) of sodium tert-butoxide and o-xylene 100 ml were refluxed under nitrogen for about overnight. Then, the solution was filtered at 100° C. To receive the filtrate, and the o-xylene was removed under reduced pressure from the filtrate. The filtrate was extracted with 100 ml dichloromethane and 500 ml water, the organic layer was dried with anhydrous magnesium sulfate, the solvent was removed and the residue was purified by column chromatography on silica (hexane-dichloromethane) to give product 3.7 g (47%) as a yellow solid. MS (m/z, $FAB^+$): 655.7; $^1H$ NMR ($CDCl_3$, 400 MHz): chemical shift (ppm) 9.12 (s, 1H), 8.81~8.73 (m, 2H), 8.66 (s, 1H), 8.25~8.19 (m, 2H), 8.13~7.89 (m, 7H), 7.56 (s, 1H), 7.48 (s, 1H), 7.01 (s, 1H), 6.98~6.91 (m, 2H), 6.84~6.75 (m, 5H), 2.28 (s, 6H), 1.83 (s, 6H), 1.81 (s, 6H).

EXAMPLE 2

Synthesis of Compound II-10

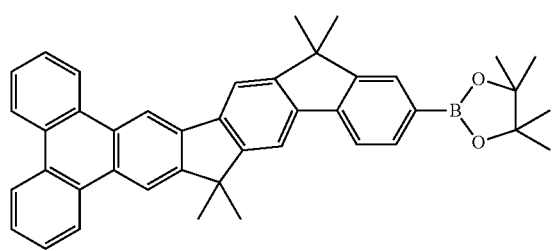

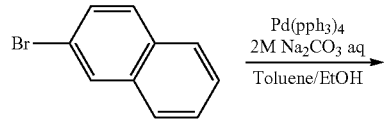

EXAMPLE 3

Synthesis of compound II-12

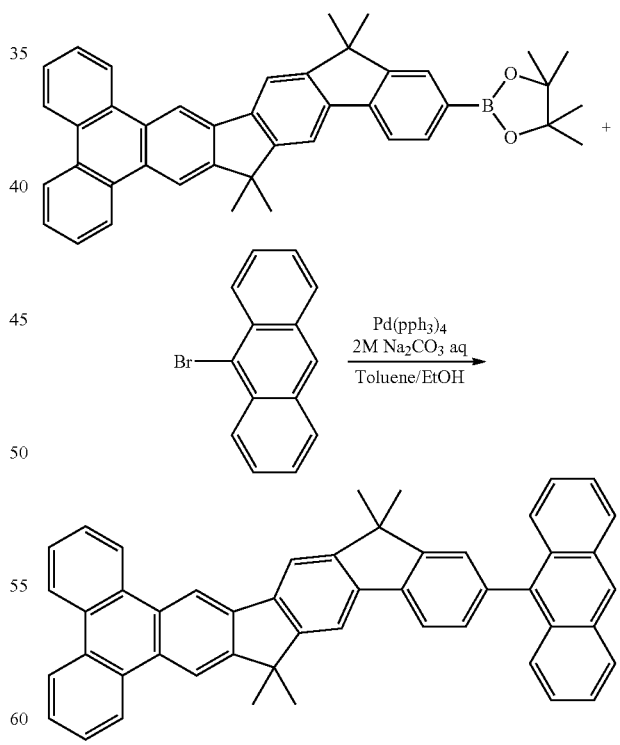

A mixture of 2.6 g (10 mmol) of 9-bromoanthracene, 7 g (12 mmol) of Intermediate II, 0.12 g (0.1 mmol) of tetrakis(triphenylphosphine)palladium, 10 ml of 2M $Na_2CO_3$, 30 ml of EtOH and 100 ml toluene was degassed and placed under nitrogen, and then heated at 90° C. for 12 h. After finishing the reaction, the mixture was allowed to cool to room temperature. Than 500 ml MeOH was added, while stirring and the precipitated product was filtered off with suction. To give 2 g (yield 32%) of yellow product which was recrystallized from toluene. MS (m/z, FAB+): 636.9; ¹H NMR (CDCl₃, 400 MHz): chemical shift (ppm) 9.13 (s, 1H), 8.78~8.70 (m, 3H), 8.68 (s, 1H), 8.42 (d, J=8.0 Hz, 1H), 8.21~7.94 (m, 3H), 7.83 (d, J=8.0 Hz, 2H), 7.79~7.57 (m, 7H), 7.43~7.36 (m, 2H), 7.31~7.26 (m, 2H), 7.17 (s, 1H), 7.06 (s, 1H), 1.82 (s, 6H), 1.80 (s, 6H).

EXAMPLE 4

Synthesis of compound II-16

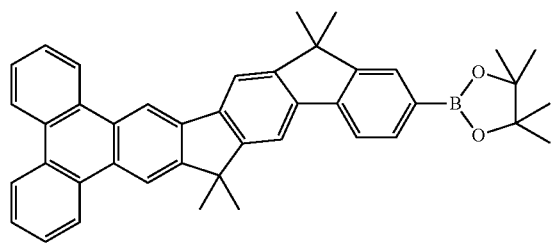

+

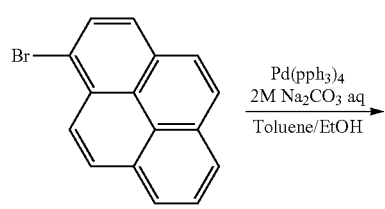 $\xrightarrow[\text{Toluene/EtOH}]{\text{Pd(pph}_3)_4 \text{ 2M Na}_2\text{CO}_3 \text{ aq}}$

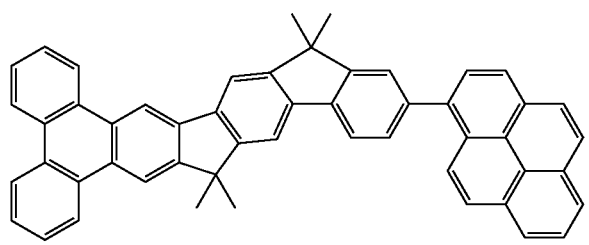

A mixture of 2.8 g (10 mmol) of 1-bromopyrene, 7 g (12 mmol) of Intermediate II, 0.12 g (0.1 mmol) of tetrakis(triphenylphosphine) palladium, 10 ml of 2M Na₂CO₃, 30 ml of EtOH and 100 ml toluene was degassed and placed under nitrogen, and then heated at 90° C. for 12 h. After finishing the reaction, the mixture was allowed to cool to room temperature. Than 500 ml MeOH was added, while stirring and the precipitated product was filtered off with suction. To give 4.1 g (yield 63%) of yellow product which was recrystallized from toluene. MS (m/z, FAB+): 660.4; ¹H NMR (CDCl₃, 400 MHz): chemical shift (ppm) 9.14 (s, 1H), 8.77~8.71 (m, 2H), 8.65 (s, 1H), 8.35~7.95 (m, 9H), 7.81~7.50 (m, 7H), 7.45 (d, J=8.0 Hz, 1H), 7.31 (d, J=8.0 Hz, 1H), 7.19 (s, 1H), 7.08 (s, 1H), 1.85 (s, 6H), 1.83 (s, 6H).

EXAMPLE 5

Synthesis of Compound III-14

Synthesis of 2-chloro-4-fluoro-N-phenylaniline

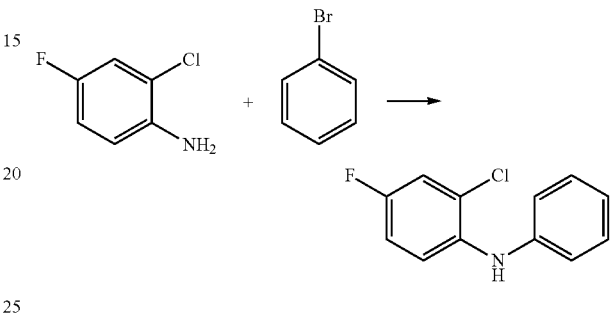

A mixture of 35 g (240 mmole) 2-chloro-4-fluoroaniline, 37.7 g (240 mmole) of bromobenzene, 0.6 g (12 mmole) of palladium (II)acetate, 4.8 g (24 mmole) of tri-tert-butylphosphine, 46 g (480 mmole) of sodium tert-butoxide and o-xylene 800 ml were refluxed under nitrogen for about overnight. Then, the solution was filtered at 100° C. To receive the filtrate, And the o-xylene was removed under reduced pressure from the filtrate. The filtrate was extracted with 500 ml dichloromethane and 2000 ml water, the organic layer was dried with anhydrous magnesium sulfate, the solvent was removed and the residue was purified by column chromatography on silica (hexane-ethyl acetate) to give product 23.4 g (44%).

Synthesis of 3-fluoro-9H-carbazole

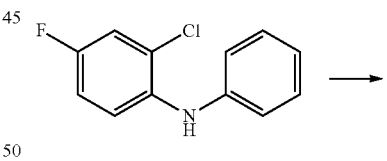 →

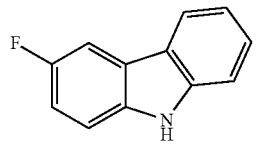

A mixture of 23.4 g (106 mmole) 2-chloro-4-fluoro-N-phenylaniline, 0.27 g (5.3 mmole) of palladium(II)acetate, 2.1 g (10.6 mmole) of tri-tert-Butylphosphine, 50.8 g (530 mmole) of sodium tert-butoxide and 1,4-dioxane 150 ml were refluxed under nitrogen for about overnight. Allowed to cool and then quenched by addition of HCl (aq) (2 M, 140 ml). The organic phase was extracted with dichloromethane and water, dried with anhydrous magnesium sulfate, the solvent was removed and the residue was purified by column chromatography on silica (hexane-ethyl acetate) to give product 6.7 g (35%)

Synthesis of 9-(dibenzo[b,d]thiophen-4-yl)-3-fluoro-9H-carbazole

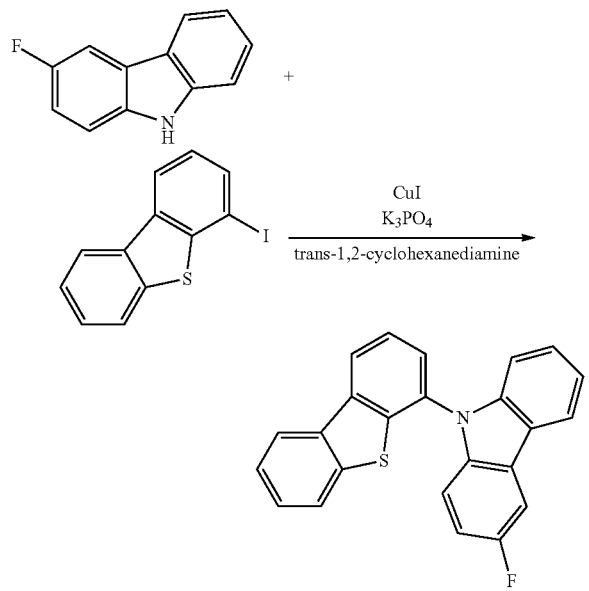

A mixture of 6.7 g (36.2 mmole) 3-fluoro-9H-carbazole, 11.2 g (36.2 mmole) of 4-iododibenzo[b,d]thiophene, 17.1 g (90 mmole) of copper(I) iodide, 19.1 g (90 mmole) of potassium phosphate, 10.3 g (90 mmole) of trans-1,2-cyclohexanediamine and 1,4-dioxane 700 ml were refluxed under nitrogen for about overnight. Then, the solution was filtered at 110° C. To receive the filtrate, And the 1,4-dioxane was removed under reduced pressure from the filtrate. The filtrate was extracted with 500 ml dichloromethane and 2000 ml water, the organic layer was dried with anhydrous magnesium sulfate, the solvent was removed and the residue was purified by column chromatography on silica (hexane-ethyl acetate) to give product 6.4 g (48%).

Synthesis of 12-(5-bromo-2-nitrophenyl)-10,10-dimethyl-10H-indeno[2,1-b]triphenylene

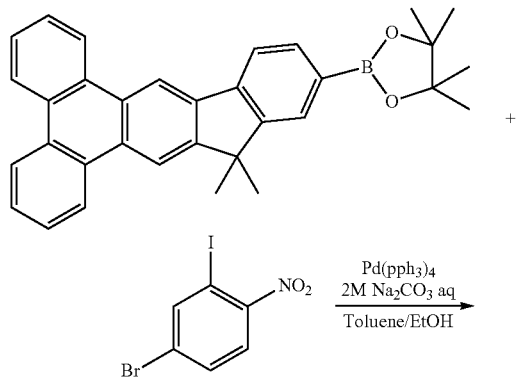

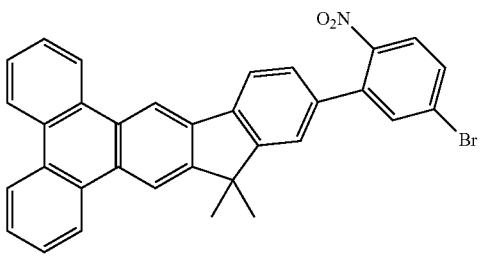

A mixture of 7.5 g (22.8 mmol) of 4-bromo-2-iodo-1-nitrobenzene, 10.7 g (22.8 mmol) of 2-(10,10-dimethyl-10H-indeno[1,2-b]triphenylen-12-yl)-4,4,5,5-tetramethyl-1,3,2-dioxaborolane, 0.29 g (0.25 mmol) of tetrakis (triphenylphosphine)palladium, 17 ml of 2M $Na_2CO_3$, 40 ml of EtOH and 100 ml toluene was degassed and placed under nitrogen, and then heated at 100° C. for 24 h. After finishing the reaction, the mixture was allowed to cool to room temperature. Than 500 ml MeOH was added, while stirring and the precipitated product was filtered off with suction. To give 7 g (yield 57%) of yellow product which was recrystallized from toluene.

Synthesis of Intermediate III

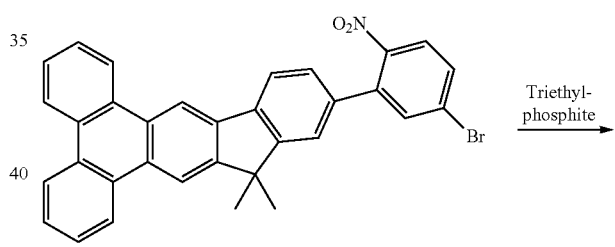

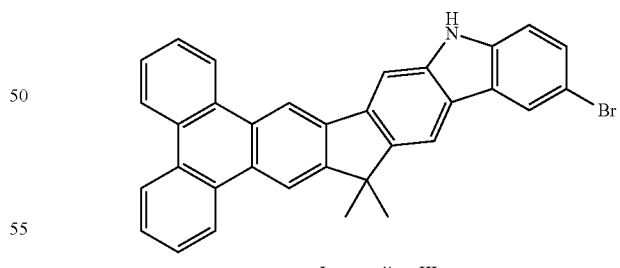

Intermediate III

A mixture of 12-(5-bromo-2-nitrophenyl)-10,10-dimethyl-10H-Indeno[2,1-b]triphenylene 7 g (12.9 mmol) and 140 ml of triethylphosphite was refluxed for 6 hours. After removal of the excess of triethylphosphite, the crude product was purified by column chromatography on silica (hexane-ethyl acetate) to give product 4.3 g (65%). $^1$H NMR ($CDCl_3$, 400 MHz): chemical shift (ppm) 9.02 (s, 1H), 8.63 (s, 1H), 8.54~8.48 (m, 2H), 8.42 (s, 1H), 8.23 (d, J=8.0 Hz, 1H), 8.07

(d, J=8.0 Hz, 1H), 7.98 (s, 1H), 7.87 (s, 1H), 7.76~7.51 (m, 5H), 7.38 (d, J=8.0 Hz, 1H), 7.28 (d, J=8.0 Hz, 1H), 1.83 (s, 6H).

Synthesis of Intermediate IV

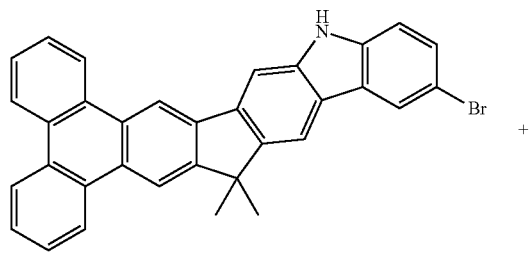

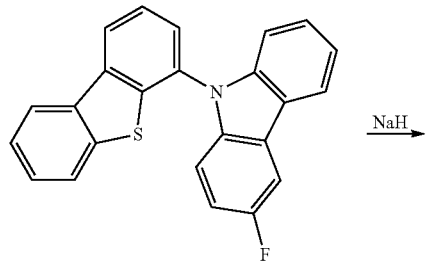

→ NaH

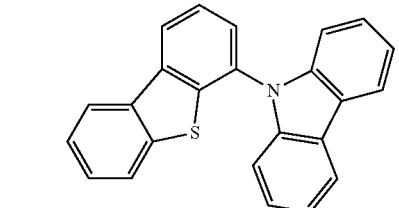

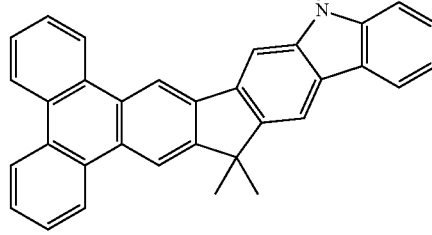

Intermediate IV 0.45 g (10 mmol) of 55% sodium hydride and 10 ml of dehydrated N,N'-dimethylformamide were placed in a 250 ml flask that had been deaerated and filled with nitrogen and stirred. A solution of Intermediate III 4.3 g (8.4 mmol) obtained immediately above in 30 ml of dehydrated N,N'-dimethylformamide was prepared and added to the contents of the flask in drops over 30 minutes. After completion of the dropwise addition, the stirring was continued for one hour. Thereafter, 3.7 g (10 mmol) of 9-(dibenzo[b,d]thiophen-4-yl)-3-fluoro-9H-carbazole was dissolved in 30 ml of dehydrated N,N'-dimethylformamide and the resulting solution was added to the contents of the flask in drops over 30 minutes. After completion of the dropwise addition, the stirring was continued for 24 hour at 50° C. After finishing the reaction, The mixture was allowed to cool to room temperature. Than 500 ml water was added, while stirring and the precipi-tated product was filtered off with suction. To give 4.9 g (yield 68%) of yellow product which was recrystallized from 1,4-dioxane.

Synthesis of Compound III-14

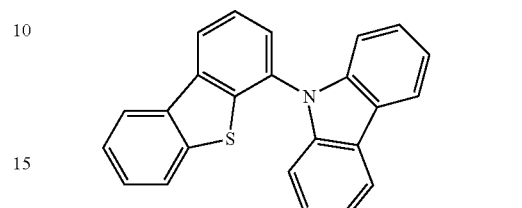

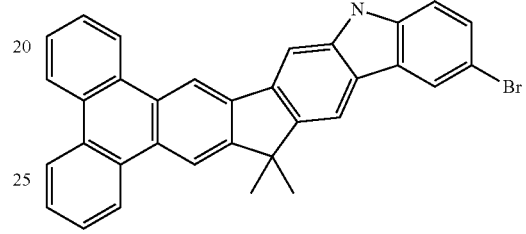

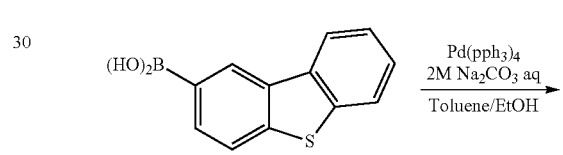 Pd(pph₃)₄ 2M Na₂CO₃ aq / Toluene/EtOH →

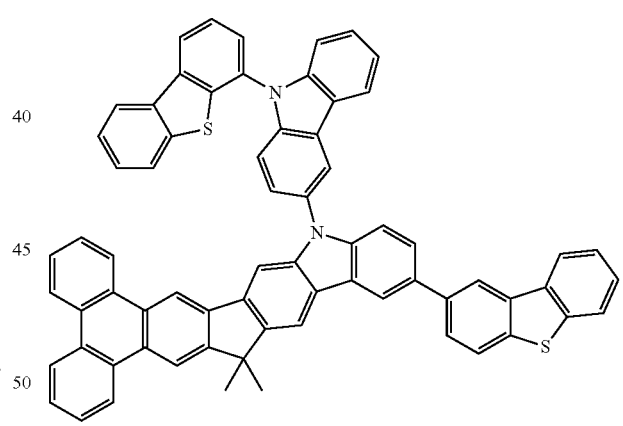

A mixture of 4.9 g (5.7 mmol) of Intermediate IV, 1.6 g (6.8 mmol) of dibenzo[b,d]thiophen-2-ylboronicacid, 0.12 g (0.1 mmol) of tetrakis(triphenylphosphine)palladium, 9 ml of 2M Na₂CO₃, 30 ml of EtOH and 100 ml toluene was degassed and placed under nitrogen, and then heated at 110° C. for 24 h. After finishing the reaction, the mixture was allowed to cool to room temperature. Than 100 ml ethyl acetate was added, while stirring and the precipitated product was filtered off with suction. To give 2.2 g (yield 41%) of yellow product which was recrystallized from toluene. MS (m/z, FAB⁺): 962.7; ¹H NMR (CDCl₃, 400 MHz): chemical shift (ppm) 9.12 (s, 1H), 8.89 (s, 1H), 8.71~8.67 (m, 2H), 8.57 (s, 1H), 8.23~7.72 (m, 11H), 7.65~7.35 (m, 17H), 7.29~7.21 (m, 2H), 7.11 (t, J=8.0 Hz, 1H), 1.85 (s, 6H).

EXAMPLE 6

Synthesis of Compound III-15

Synthesis of 3-bromo-9-(dibenzo[b,d]furan-2-yl)-9H-carbazole

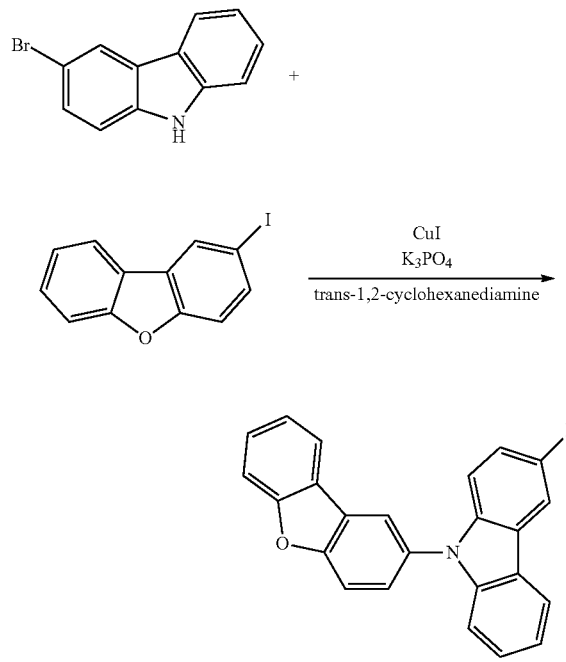

A mixture of 8.9 g (36.2 mmole) 3-bromo-9H-carbazole, 10.6 g (36.2 mmole) of 2-iododibenzo[b,d]furan, 17.1 g (90 mmole) of copper(I) iodide, 19.1 g (90 mmole) of potassium phosphate, 10.3 g (90 mmole) of trans-1,2-cyclohexanediamine and 1,4-dioxane 700 ml were refluxed under nitrogen for about overnight. Then, the solution was filtered at 110° C. To receive the filtrate, And the 1,4-dioxane was removed under reduced pressure from the filtrate. The filtrate was extracted with 500 ml dichloromethane and 2000 ml water, the organic layer was dried with anhydrous magnesium sulfate, the solvent was removed and the residue was purified by column chromatography on silica (hexane-ethyl acetate) to give product 8.4 g (56%).

Synthesis of 9-(dibenzo[b,d]furan-2-yl)-3-(4,4,5,5-tetramethyl-1,3,2-dioxaborolan-2-yl)-9H-carbazole

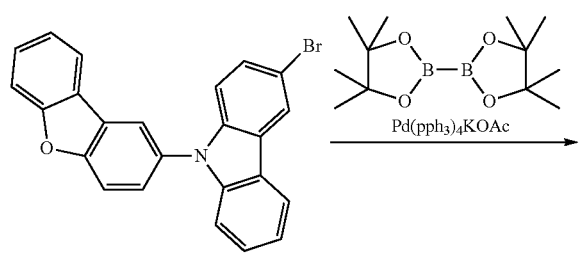

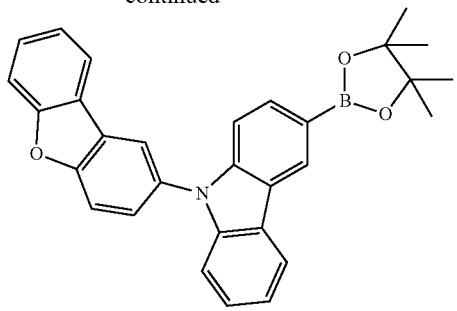

A mixture of 8.4 g (20.4 mmol) of 3-bromo-9-(dibenzo[b,d]Furan-2-yl)-9H-carbazole, 6.6 g (26 mmol) of bis(pinacolato)diboron, 0.3 g (0.26 mmol) of tetrakis(triphenylphosphine)palladium, 2.7 g (28 mmol) of potassium acetate, and 300 ml 1,4dioxane was degassed and placed under nitrogen, and then heated at 90° C. for 24 hours. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product 7.1 g (76%).

Synthesis of Intermediate V

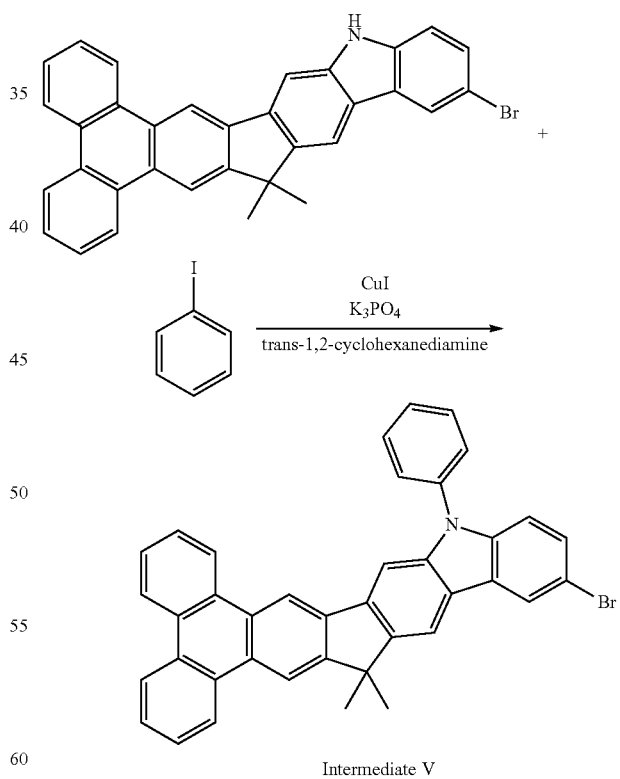

Intermediate V

A mixture of 18.6 g (23.1 mmole) Intermediate III, 7.3 g (36.2 mmole) of iodobenzene, 17.1 g (90 mmole) of copper(I) iodide, 19.1 g (90 mmole) of potassium phosphate, 10.3 g (90 mmole) of trans-1,2-cyclohexanediamine and 1,4-dioxane 500 ml were refluxed under nitrogen for about overnight.

Then, the solution was filtered at 110° C. To receive the filtrate, And the 1,4-dioxane was removed under reduced pressure from the filtrate. The filtrate was extracted with 500 ml dichloromethane and 2000 ml water, the organic layer was dried with anhydrous magnesium sulfate, the solvent was removed and the residue was purified by column chromatography on silica (hexane-ethylacetate) to give product 13.6 g (64%).

Synthesis of Intermediate Compound III-15

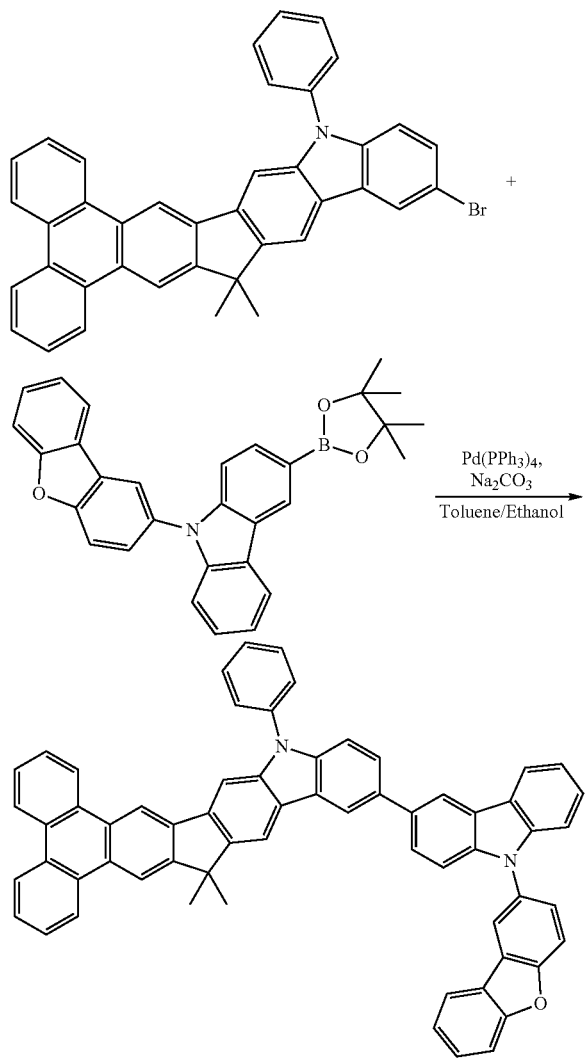

A mixture of 13.6 g (23.1 mmol) of Intermediate V, 10.8 g (23.1 mmol) of 9-(dibenzo[b,d]furan-2-yl)-3-(4,4,5,5-tetramethyl-1,3,2-dioxaborolan-2-yl-9H-carbazole, 0.29 g (0.25 mmol) of tetrakis(triphenylphosphine)palladium, 30 ml of 2M Na$_2$CO$_3$, 60 ml of EtOH and 200 ml toluene was degassed and placed under nitrogen, and then heated at 100° C. for 24 h. After finishing the reaction, the mixture was allowed to cool to room temperature. Than 100 ml ethyl acetate was added, while stirring and the precipitated product was filtered off with suction. To give 9.5 g (yield 49%) of yellow product which was recrystallized from toluene. MS (m/z, FAB$^+$): 840.9; $^1$H NMR (CDCl$_3$, 400 MHz): chemical shift (ppm) 9.08 (s, 1H), 8.87 (s, 1H), 8.69~8.65 (m, 2H), 8.24~8.01 (m, 3H), 7.86 (s, 1H), 7.85~7.74 (m, 3H), 7.78~7.48 (m, 12H), 7.42~7.25 (m, 8H), 7.10 (d, J=8.0 Hz, 1H), 7.04~6.98 (m, 2H), 1.83 (s, 6H).

General Method of Producing Oleds

ITO-coated glasses with 12 ohm/square in Resistance and 120 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100)

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a guest material. This is achieved by co-vaporization from two or more sources.

Dipyrazino[2,3-f:2',3'-h]quinoxaline-2,3,6,7,10,1-hexacarbonitrile (Hat-CN) is used as hole injection layer in this organic EL device. N,N-Bis(naphthalene-1-yl)-N,N'-bis(phenyl)-benzidine (NPB) is most widely used as the hole transporting layer and 2,9-bis(naphthalene-2-yl)-4,7-diphenyl-1,10-phenanthroline (NBphen) is used as electron transporting material in organic EL device for its high thermal stability and long life-time than BPhen or BCP. For fluorescent emitting device, 1,1'-(9,9-dimethyl-9H-fluorene-2,7-diyl)dipyrene (DFDP) is used as emissive host and (E)-6-(4-(diphenylamino) styryl)-N,N-diphenylnaphthalen-2-amine (D1) is used as fluorescent dopant. For phosphorescent emitting device, Bis(2-methyl-8-quinolinolate)-4-(phenylphenolato)aluminium (BAlq) is used as host of emitting layer and Tris(1-phenylisoquinoline)Iridium(III)Ir(piq)$_3$), Tris(2-phenylquinoline)iridium (III)(Ir(2-phq)$_3$) are used as phosphorescent dopant. The prior art of OLED materials for producing standard organic EL device and comparable material in this invention shown its chemical structure as following:

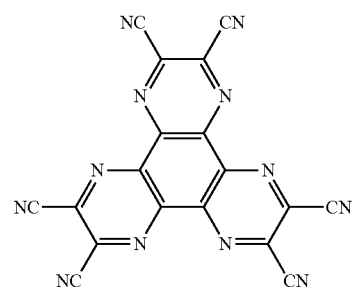

HAT-CN

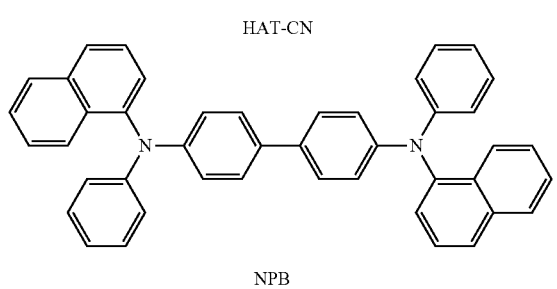

NPB

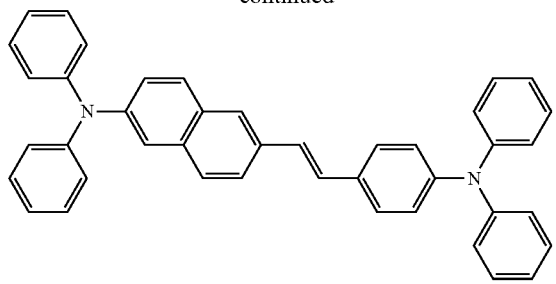

D1

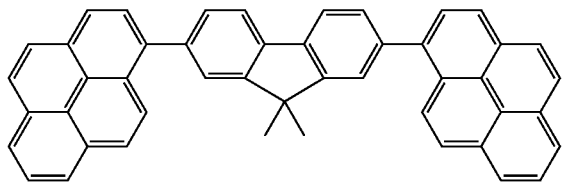

DFDP

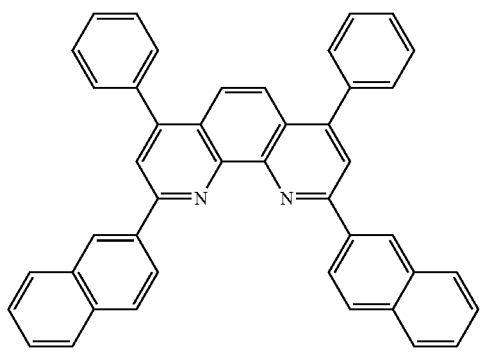

NBphen

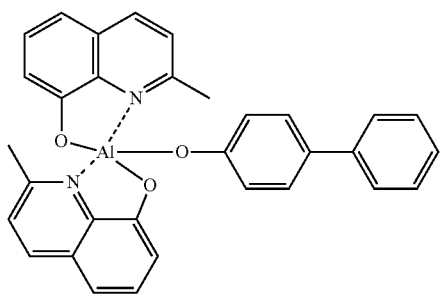

BAlq

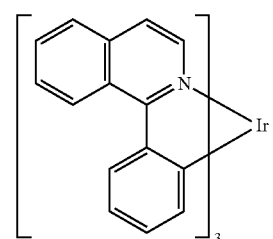

Ir(piq)₃

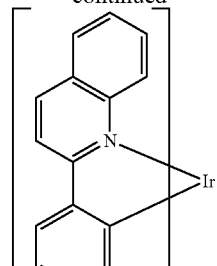

Ir(2-phq)₃

A typical OLED consists of low work function metals, such as Al, Mg, Ca, Li and K, as the cathode by thermal evaporation, and the low work function metals can help electrons injecting the electron transporting layer from cathode. In addition, for reducing the electron injection barrier and improving the OLED performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the OLEDs fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 7

Using a procedure analogous to the abovementioned general method, fluorescent blue-emitting organic EL device having the following device structure were produced (See FIG. 1): ITO/HAT-CN (20 nm)/NPB (50 nm)/fluorescent blue host+5% dopant (30 nm)/NPhen (30 nm)/LiF (0.5 nm)/Al (160 nm). The I-V-B and half-life time of fluorescent blue-emitting organic EL device testing report as Table 1, The half-life time is defined that the initial luminance of 3000 $cd/m^2$ has dropped to half.

TABLE 1

| Fluorescent blue host + 5% dopant | Voltage (V) | Luminance $(cd/m^2)$ | Yield (cd/A) | CIE (y) | Half-lifetime (hr) Initial luminance = 3000 $(cd/m^2)$ |
|---|---|---|---|---|---|
| DFDP + D1 | 6 | 950 | 4.92 | 0.17 | 220 |
| DFDP + II-2 | 6 | 1080 | 3.92 | 0.13 | 280 |
| DFDP + II-5 | 6 | 1010 | 4.41 | 0.14 | 210 |
| DFDP + II-7 | 6 | 1020 | 4.72 | 0.12 | 330 |
| II-10 + D1 | 6 | 1580 | 3.32 | 0.14 | 260 |
| II-12 + D1 | 6 | 1460 | 4.89 | 0.15 | 300 |
| II-16 + D1 | 6 | 1710 | 5.25 | 0.15 | 460 |
| II-16 + II-7 | 6 | 1520 | 5.07 | 0.13 | 440 |

In the above preferred embodiments, we show organic material formula(II) used as fluorescent blue host or dopant than comparable example DFDP and D1 with higher half-life time and practical operation durability. Higher luminance than comparable DFDP has also been achieved at a driving voltage of 6V using the mentioned organic material for blue-emitting organic EL devices. The efficiency of most present invention examples show over 4 cd/A and appears CIE(y) are between 0.13 and 0.15 comparable with prior art DFDP and D1 (CIE(y)=0.17). The organic material formula(II) can be used as fluorescent blue host or dopant.

EXAMPLE 8

Using a procedure analogous to the abovementioned general method, phosphorescent emitting organic EL device having the following device structure were produced (See FIG. 1.): ITO/HAT-CN (20 nm)/NPB (50 nm)/phosphorescent host+10% dopant (30 nm)/NPhen (30 nm)/LiF (0.5 nm)/Al (160 nm). The I-V-B and half-life time of phosphorescent emitting organic EL device testing report as Table 2, The half-lifetme is defined that the initial luminance of 3000 cd/m² has dropped to half.

TABLE 2

| Phosphorescent host + 10% dopant | Voltage (V) | Luminance (cd/m²) | Yield (cd/A) | Device color | Half-lifetime (hr) Initial luminance = 3000 (cd/m²) |
|---|---|---|---|---|---|
| BAlq + Ir(piq)₃ | 6 | 650 | 7.96 | red | 360 |
| BAlq + Ir(phq)₃ | 6 | 480 | 13.83 | orange | 380 |
| III-14 + Ir(piq)₃ | 6 | 910 | 8.68 | red | 610 |
| III-14 + Ir(phq)₃ | 6 | 1320 | 15.72 | yellow | 930 |
| III-15 + Ir(piq)₃ | 6 | 880 | 8.32 | red | 580 |
| III-15 + Ir(phq)₃ | 6 | 1100 | 16.89 | yellow | 870 |

In the above preferred embodiments, we show organic material formula(II) used as phosphorescent host than comparable example BAlq with higher half-life time and practical operation durability. Higher luminance and efficiency than comparable BAlq has also been achieved at a driving voltage of 6V using the mentioned organic material for phosphorescent organic EL devices. The organic material formula(II) can be used as phosphorescent organic EL devices for practice use.

To sum up, the present invention discloses a organic compound which can be used for organic EL device is disclosed. The mentioned organic compound are represented by the following formula(I).

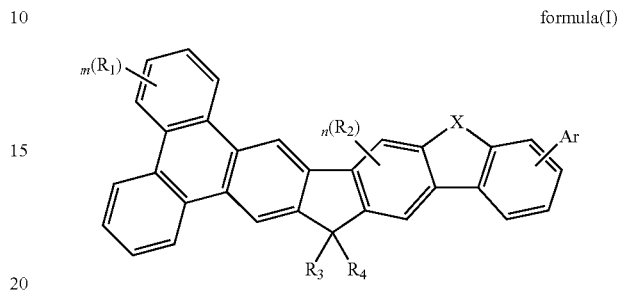

formula(I)

m represent an integer of 0 to 10, n represent an integer of 0 to 2. X is a divalent bridge selected from the atom or group consisting from O, S, C(R₅)₂, N(R₅), Si(R₅)₂. Ar represent a hydrogen atom, a halide, a substituted or unsubstituted arylamine group, a substituted or unsubstituted aryl group system having 5 to 50 aromatic ring atoms, a substituted or unsubstituted heteroaryl ring system having 5 to 50 aromatic ring atoms and each aromatic ring to form a mono or polycyclic ring system. $R_1$ to $R_5$ are identical or different. $R_1$ to $R_5$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

What is claimed is:
1. A organic compound with a general formula(I) as following:

formula(I)

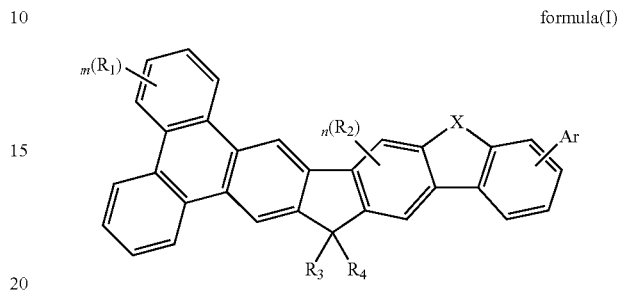

m represent an integer of 0 to 10, n represent an integer of 0 to 2; X is a divalent bridge selected from the atom or group consisting from O, S, C(R₅)₂, N(R₅), Si(R₅)₂; Ar represent a hydrogen atom, a halide, a substituted or unsubstituted arylamine group, a substituted or unsubstituted aryl group system having 5 to 50 aromatic ring atoms, a substituted or unsubstituted heteroaryl ring system having 5 to 50 aromatic ring atoms and each aromatic ring to form a mono or polycyclic ring system; $R_1$ to $R_5$ are identical or different; $R_1$ to $R_5$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

2. According to claim 1, the organic compound formula(I) used as fluorescent host material or dopant material of emitting layer is represented by the following formula(II):

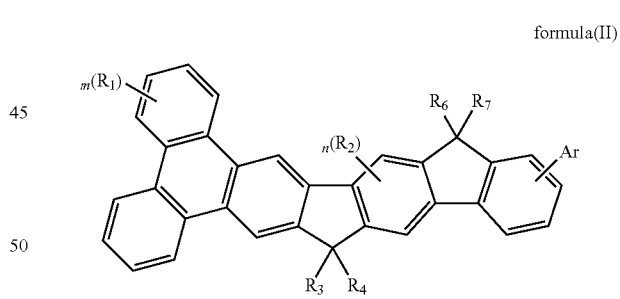

formula(II)

m represent an integer of 0 to 10, n represent an integer of 0 to 2; Ar represent a hydrogen atom, a halide, a substituted or unsubstituted arylamine group, a substituted or unsubstituted aryl group system having 5 to 50 aromatic ring atoms, a substituted or unsubstituted heteroaryl ring system having 5 to 50 aromatic ring atoms and each aromatic ring to form a mono or polycyclic ring system; $R_1$ to $R_4$ and $R_6$ to $R_7$ are identical or different; $R_1$ to $R_4$ and $R_6$ to $R_7$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

3. According to claim 2, the Ar group represented as the following:
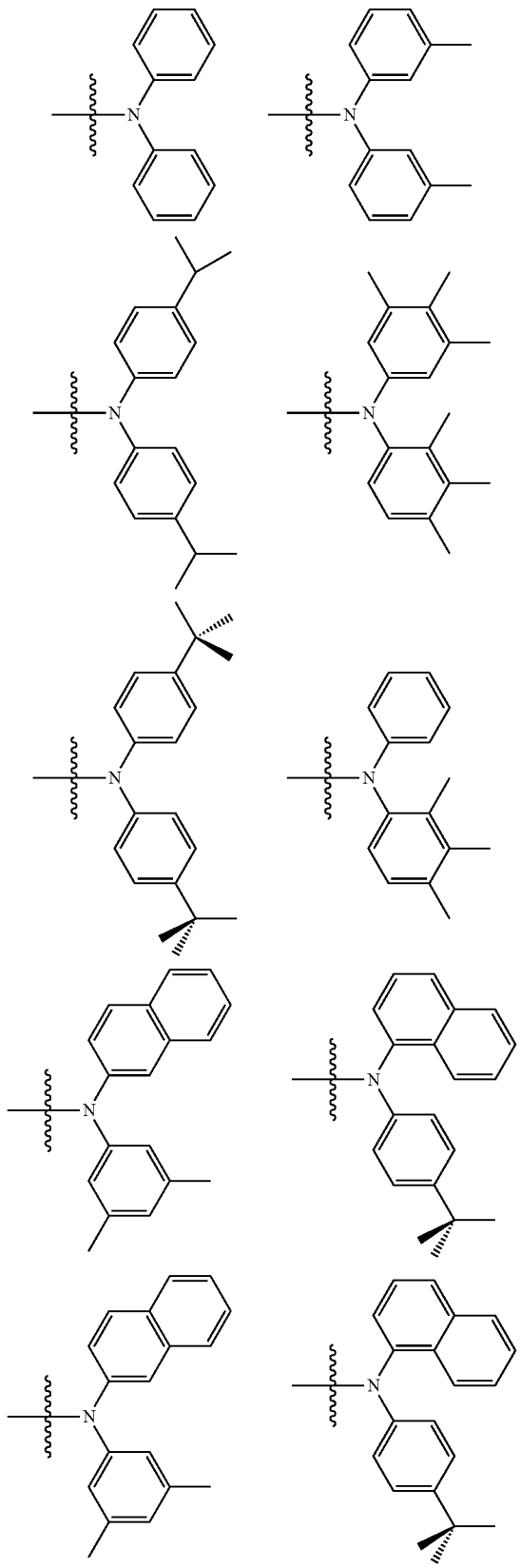
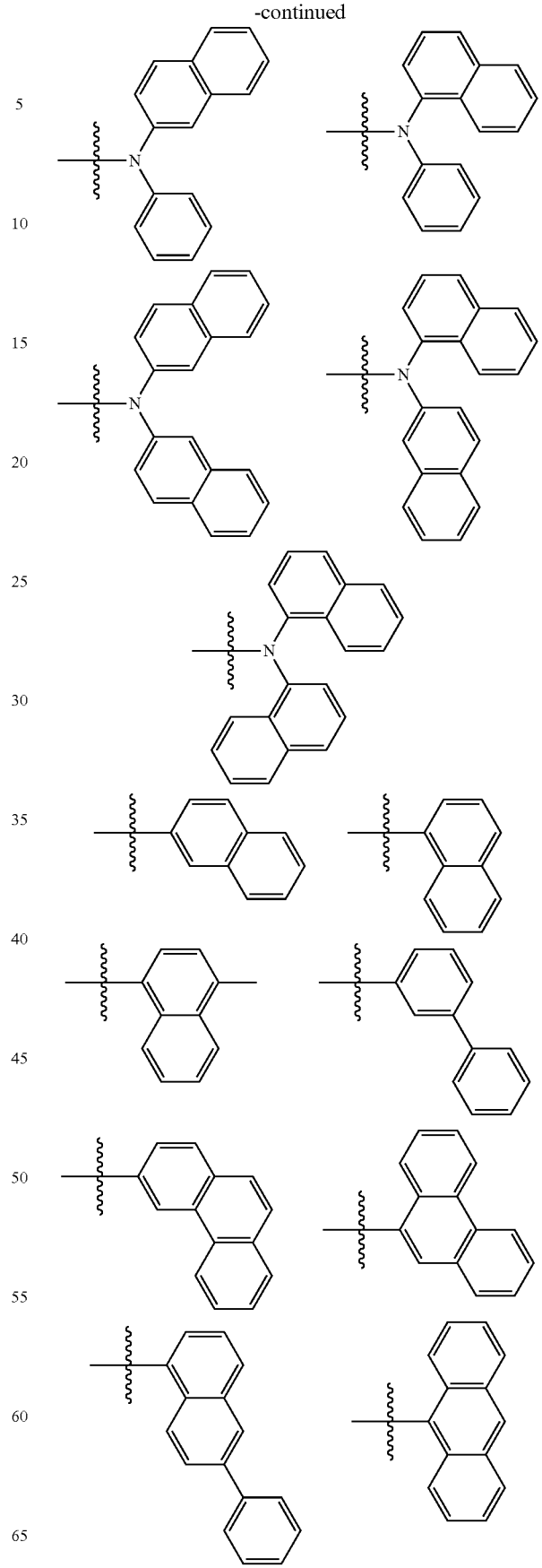
-continued -continued

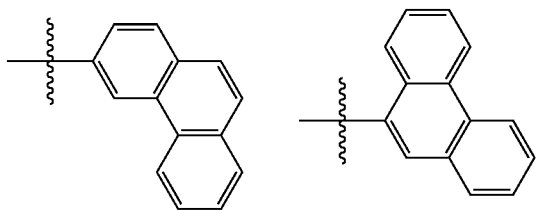
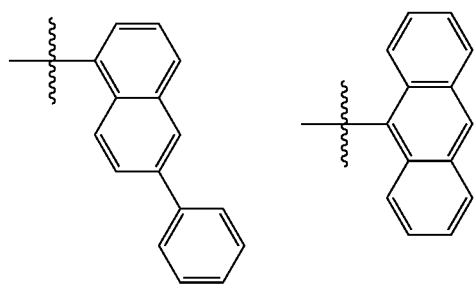
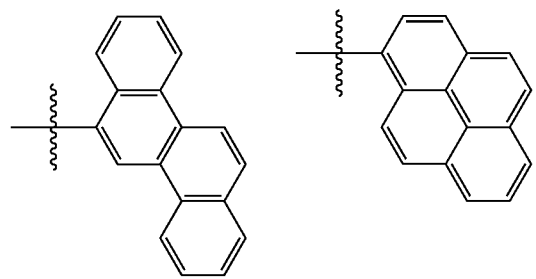
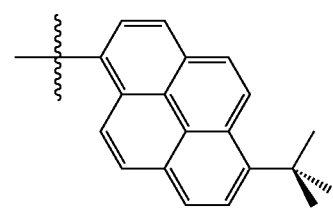
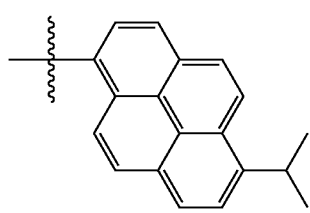
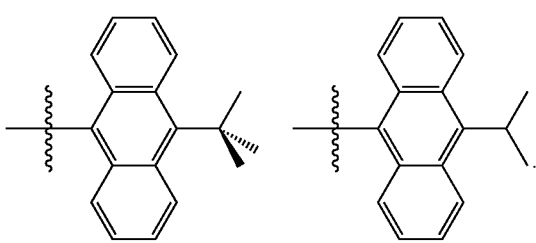

4. According to claim 1, the organic compound formula(I) used as phosphorescent host material of emitting layer is represented by the following formula(III):

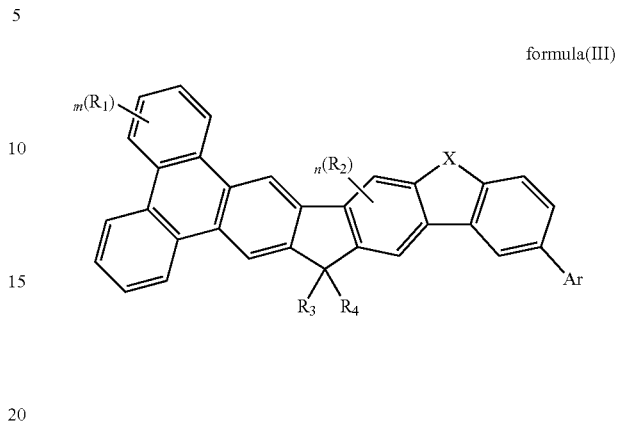

formula(III)

wherein m represent an integer of 0 to 10, n represent an integer of 0 to 2; X is a divalent bridge selected from the atom or group consisting from O, S, $N(R_5)$; Ar represented a substituted or unsubstituted aryl group system having 5 to 50 aromatic ring atoms, a substituted or unsubstituted heteroaryl ring system having 5 to 50 aromatic ring atoms to form a mono or polycyclic ring system; $R_1$ to $R_5$ are identical or different; $R_1$ to $R_5$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

5. According to claim 4, the Ar or $R_5$ group are represented as the following:

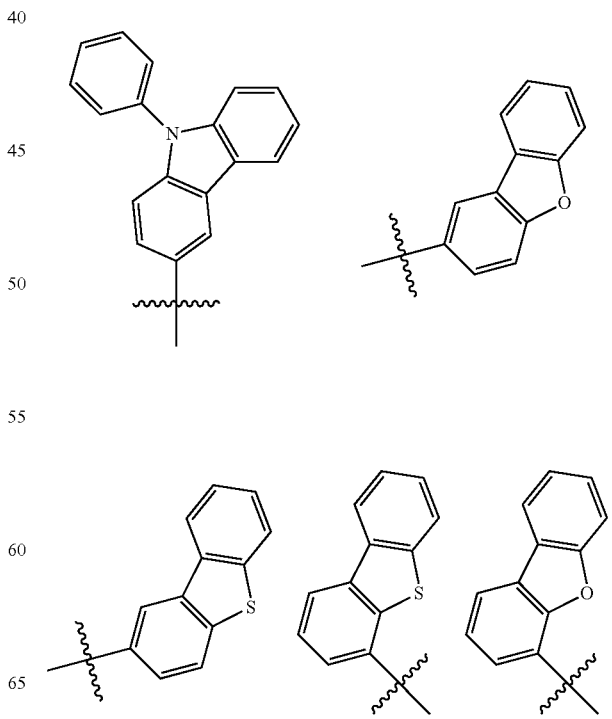

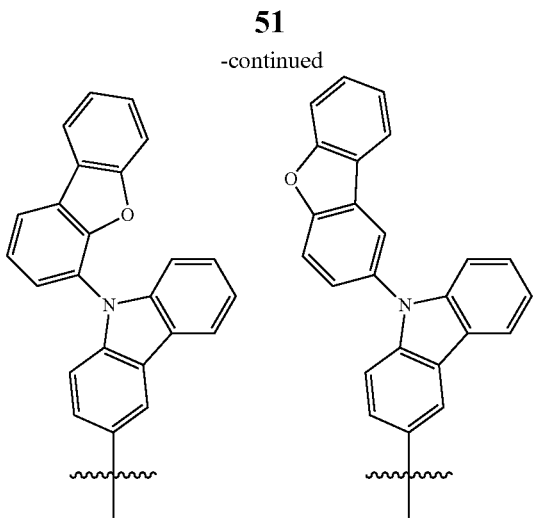

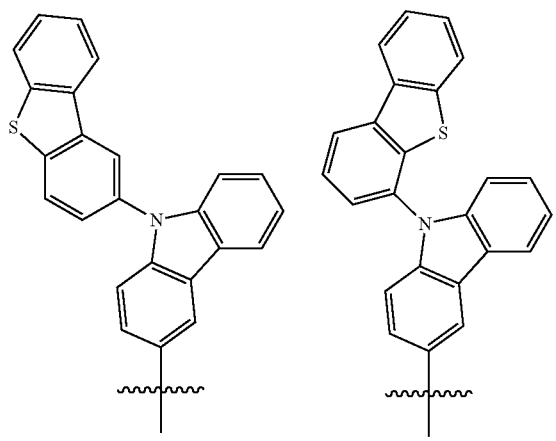

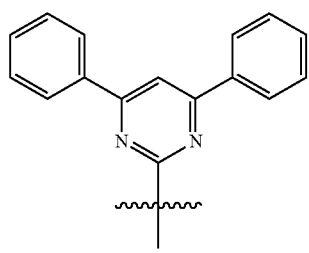 [SMILES: *c1nc(-c2ccccc2)nc(-c2ccccc2)n1]

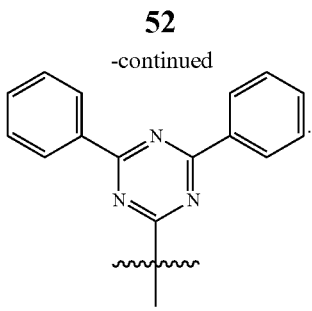

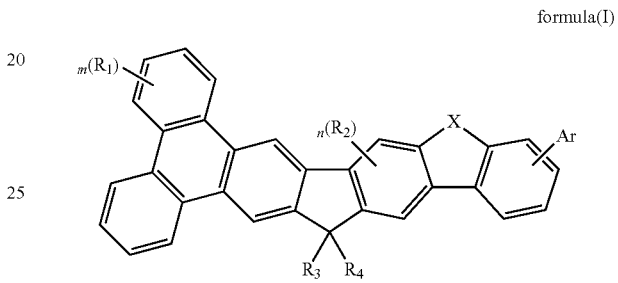

6. A organic EL device comprising a pair of electrodes consisting of a cathode and an anode and between the pairs of electrodes comprising a layer of organic compound with a general formula(I) as following:

formula(I)

m represent an integer of 0 to 10, n represent an integer of 0 to 2; X is a divalent bridge selected from the atom or group consisting from O, S, C($R_5$)$_2$, N($R_5$), Si($R_5$)$_2$; Ar represent a hydrogen atom, a halide, a substituted or unsubstituted arylamine group, a substituted or unsubstituted aryl group system having 5 to 50 aromatic ring atoms, a substituted or unsubstituted heteroaryl ring system having 5 to 50 aromatic ring atoms and each aromatic ring to form a mono or polycyclic ring system; $R_1$ to $R_5$ are identical or different; $R_1$ to $R_5$ are independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 6 to 30 carbon atoms.

7. According to claim 6, an organic EL device comprising a layer of organic compound and functions as host material or dopant material of emitting layer and/or as electron transporting material of a light emitting layer.

8. According to claim 7, an organic EL device comprising a layer of organic compound and functions as fluorescent blue emitting host or dopant material of a light emitting layer.

9. According to claim 7, an organic EL device comprising a layer of organic compound and function as phosphorescent host material of a light emitting layer.

* * * * *